(12) United States Patent
Takahashi et al.

(10) Patent No.: US 10,768,095 B2
(45) Date of Patent: Sep. 8, 2020

(54) OPTICAL SENSOR

(71) Applicants: Yoichiro Takahashi, Tokyo (JP); Takeaki Shimokawa, Kyoto (JP); Toshihiro Ishii, Miyagi (JP)

(72) Inventors: Yoichiro Takahashi, Tokyo (JP); Takeaki Shimokawa, Kyoto (JP); Toshihiro Ishii, Miyagi (JP)

(73) Assignees: Ricoh Company, Ltd, Tokyo (JP); ADVANCED TELECOMMUNICATIONS RESEARCH INSTITUTE INTERNATIONAL, Kyoto (JP)

( * ) Notice: Subject to any disclaimer, the term of this patent is extended or adjusted under 35 U.S.C. 154(b) by 0 days.

(21) Appl. No.: 16/506,160

(22) Filed: Jul. 9, 2019

(65) Prior Publication Data

US 2020/0064253 A1 Feb. 27, 2020

(30) Foreign Application Priority Data

Aug. 23, 2018 (JP) .................................. 2018-156659

(51) Int. Cl.
*G01N 21/01* (2006.01)
*G01N 21/17* (2006.01)
*A61B 5/1455* (2006.01)

(52) U.S. Cl.
CPC ............. *G01N 21/01* (2013.01); *G01N 21/17* (2013.01); *A61B 5/14552* (2013.01); *A61B 2562/0233* (2013.01); *G01N 2201/06* (2013.01)

(58) Field of Classification Search
CPC .... G01N 21/01; G01N 21/4795; G01N 21/49; G01N 21/03; G01N 21/314; G01N 21/532; G01N 21/3151; G01N 21/17; G01N 2201/0662; A61B 5/4552; A61B 5/681; A61B 5/14552; A61B 2562/0242; A61B 2562/0238; A61B 2562/043
USPC ...... 356/432–440, 237.1–237.5, 73; 250/574
See application file for complete search history.

(56) References Cited

U.S. PATENT DOCUMENTS

| 6,353,226 | B1 * | 3/2002 | Khalil ................ A61B 5/14532 250/339.11 |
| 10,039,452 | B2 | 8/2018 | Ishii et al. |
| 10,067,056 | B2 | 9/2018 | Fujiwara et al. |
| 10,175,169 | B2 | 1/2019 | Ishii et al. |

(Continued)

FOREIGN PATENT DOCUMENTS

| JP | 2010-005047 | 1/2010 |
| JP | 4697000 | 6/2011 |

(Continued)

*Primary Examiner* — Hoa Q Pham
(74) *Attorney, Agent, or Firm* — IPUSA, PLLC

(57) ABSTRACT

An optical sensor includes a light emitter configured to irradiate a surface of an object with a plurality of non-parallel light beams, a light detector configured to detect a plurality of light beams that have been reflected within the object and have returned to the surface from a plurality of directions, a recording unit configured to store pre-calculated results of a plurality of models having different optical properties and physical structures, and a calculating unit configured to calculate a light amount ratio of the plurality of reflected light beams, and estimate an optical property of the object based on the calculated light amount ratio and the pre-calculated results.

10 Claims, 27 Drawing Sheets

(56) References Cited

U.S. PATENT DOCUMENTS

| | | | |
|---|---|---|---|
| 10,177,530 B2 | 1/2019 | Ishii et al. | |
| 10,292,590 B2 | 5/2019 | Ishii et al. | |
| 2002/0084417 A1* | 7/2002 | Khalil | G01N 21/49 250/341.8 |
| 2006/0184047 A1* | 8/2006 | Yamashita | A61B 5/14552 600/476 |
| 2014/0251533 A1* | 9/2014 | Lim | B23K 26/0626 156/247 |
| 2017/0251963 A1 | 9/2017 | Hashimoto et al. | |

FOREIGN PATENT DOCUMENTS

| | | |
|---|---|---|
| JP | 2011-220993 | 11/2011 |
| JP | 5202736 | 6/2013 |
| JP | 5565837 | 8/2014 |
| JP | 2015-092151 | 5/2015 |
| JP | 2015-175684 | 10/2015 |
| JP | 2016-002164 | 1/2016 |
| JP | 2016-010717 | 1/2016 |
| JP | 2016-093280 | 5/2016 |
| JP | 2016-128802 | 7/2016 |
| JP | 2016-130669 | 7/2016 |
| JP | 2016-130705 | 7/2016 |
| JP | 2016-211936 | 12/2016 |
| JP | 2017-003563 | 1/2017 |
| JP | 2017-117891 | 6/2017 |
| JP | 2017-153876 | 9/2017 |

\* cited by examiner

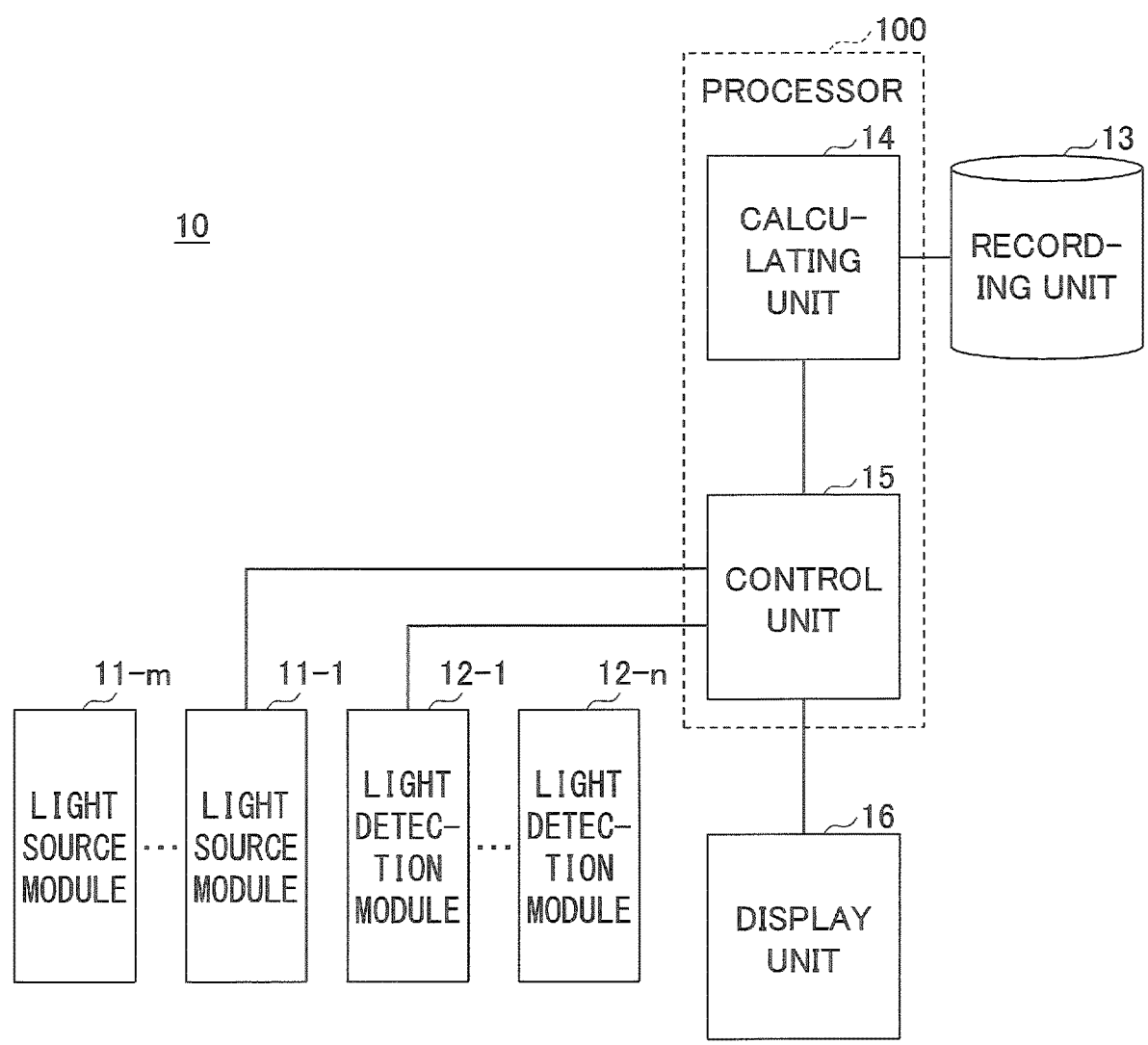

INDIVIDUAL CONNECTION

DAISY CHAIN CONNECTION

35
MODULE INSTALLATION POSITION

- LIGHT SOURCE MODULE 11
- LIGHT DETECTION MODULE 12

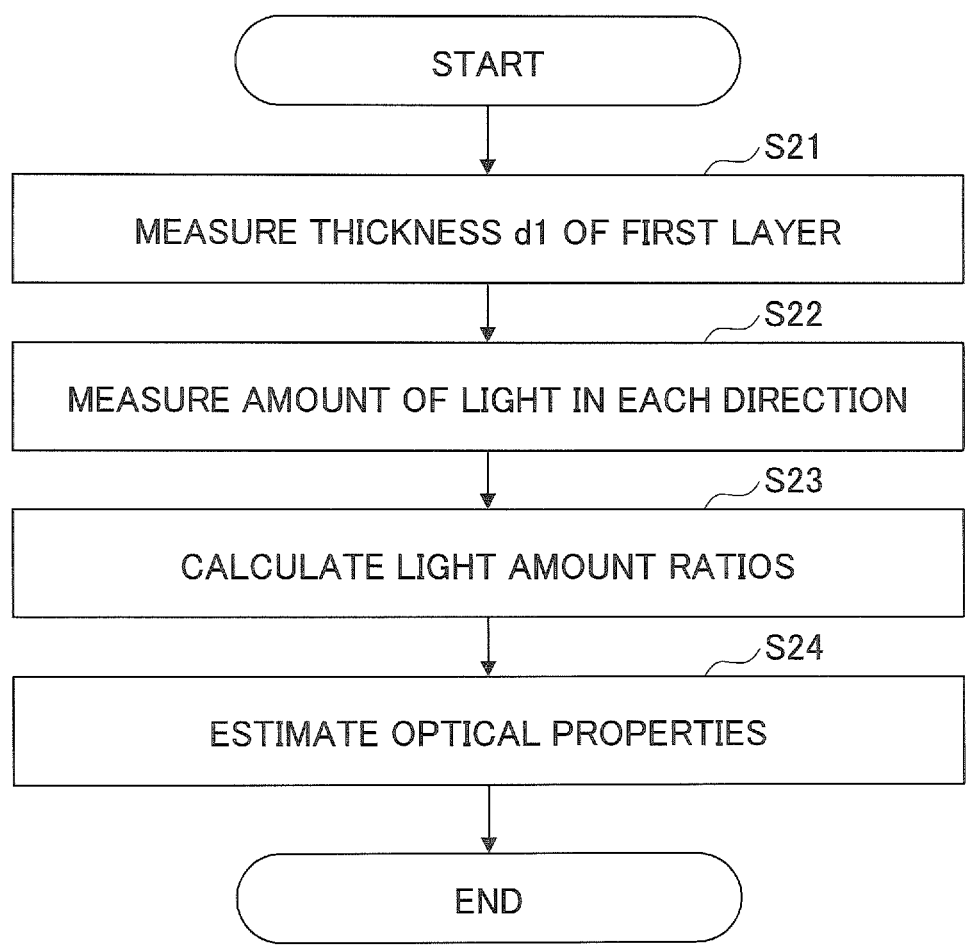

d2 (CSF) = 3 mm d2 (CSF) = 7 mm d2 (CSF) = 3 mm d2 (CSF) = 7 mm

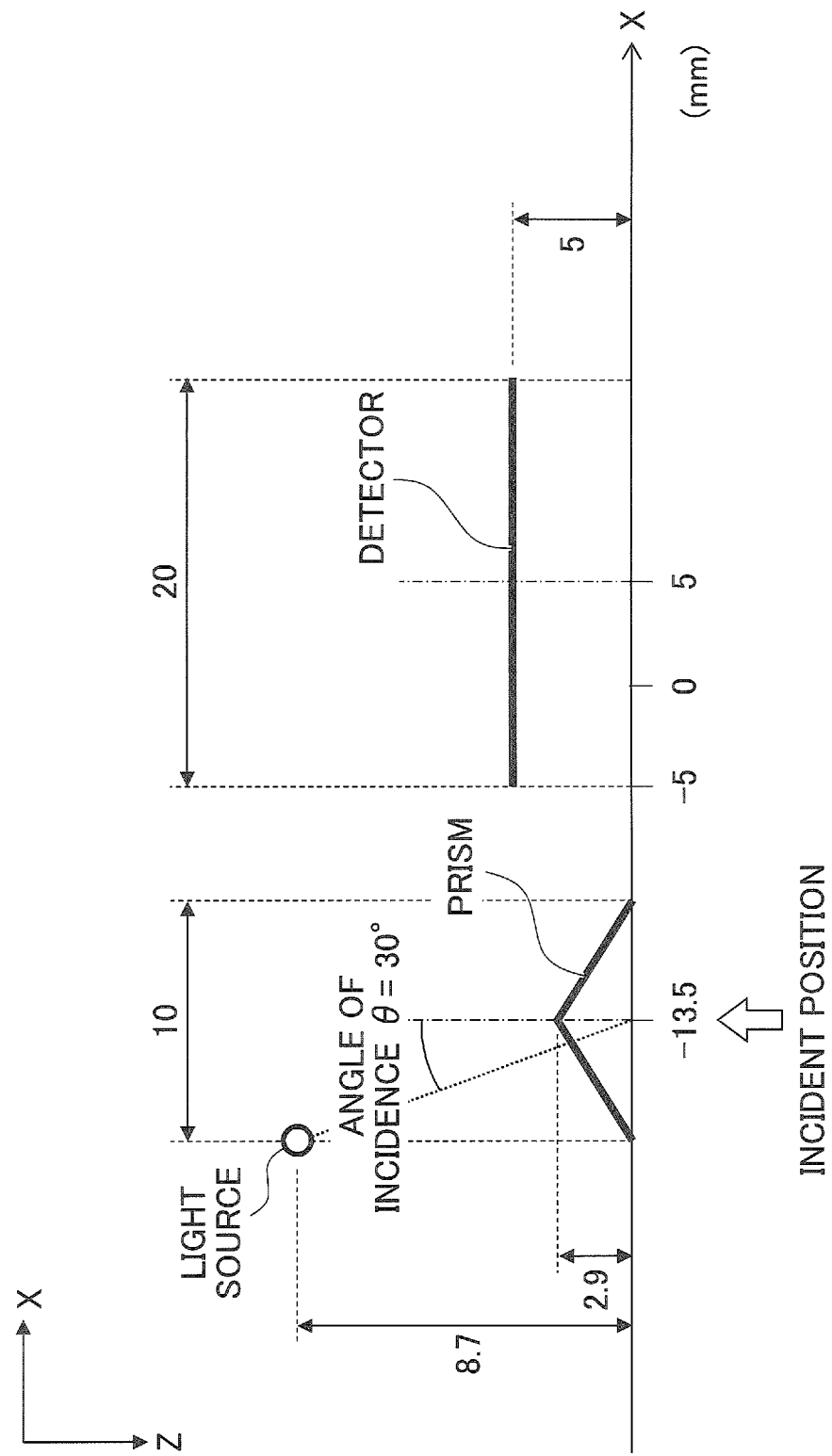

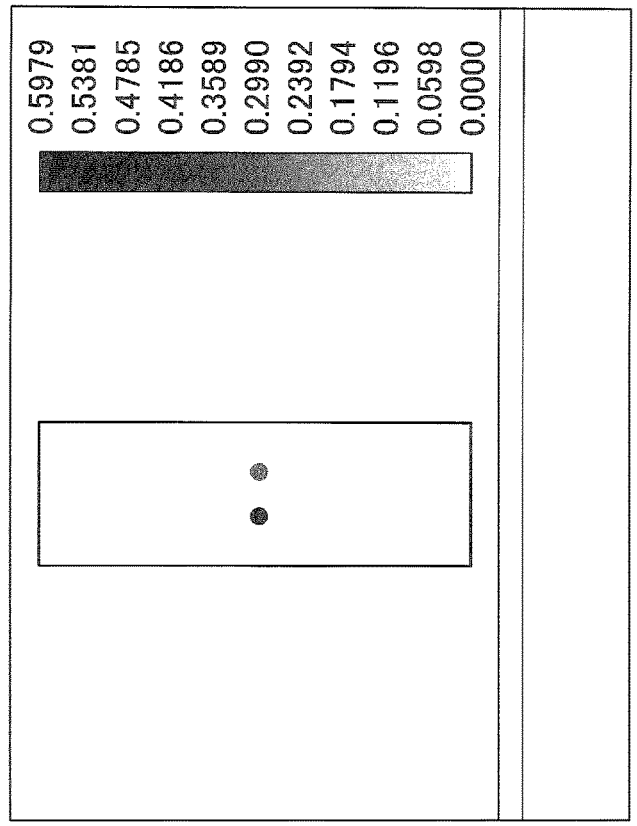
FIG.28B S-POLARIZED LIGHT
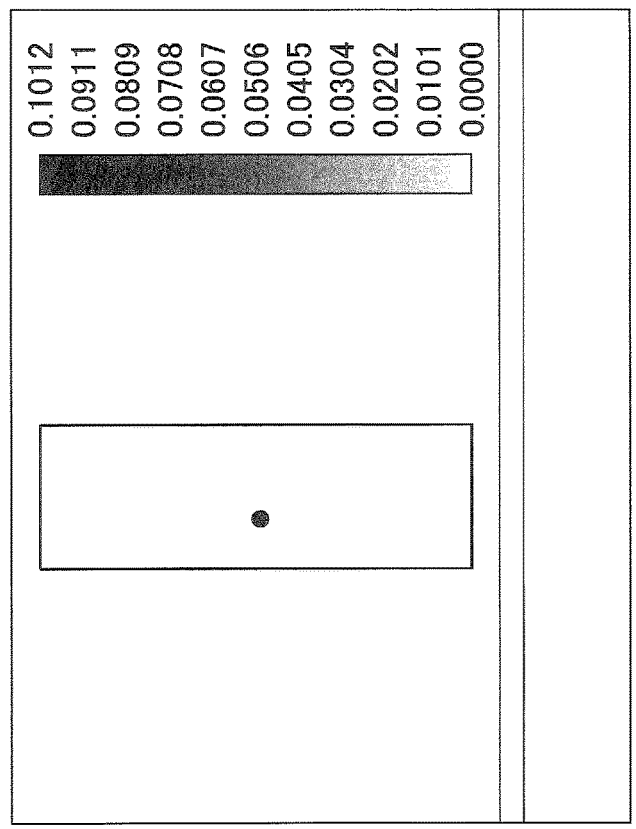
FIG.28A P-POLARIZED LIGHT

P-POLARIZED LIGHT

S-POLARIZED LIGHT

NO FOREIGN SUBSTANCE IS PRESENT

FOREIGN SUBSTANCE PRESENTS

OPTICAL SENSOR

CROSS-REFERENCE TO RELATED APPLICATION

The present application claims priority under 35 U.S.C. § 119 to Japanese Patent Application No. 2018-156659, filed on Aug. 23, 2018, the entire contents of which are incorporated herein by reference.

BACKGROUND OF THE INVENTION

1. Field of the Invention

The disclosures herein generally relate to an optical sensor that measures optical properties.

2. Description of the Related Art

As a method for measuring optical properties inherent in the interaction between light and matter, there exists a method for determining optical properties by combining values measured by an integrating sphere and simulated values. In this method, after a sample is placed in a device, the amount of reflected light and the amount of transmitted light are measured at each angle by slightly changing the angle of emitted light. Then, the measured results are combined and the reflectance and transmittance are determined. In order to estimate optical properties based on experimental results, a Monte Carlo simulation is performed by using candidate optical properties, and it is determined whether the measured values match the simulated reflectance and transmittance values. If there is a mismatch, comparisons are repeatedly performed by changing values.

Further, there exists a method for comparing measured values to simulated sensitivity distribution values, and using the most approximate sensitivity distribution. However, sensitivity distribution is affected not only by optical properties, but also by physical structures. Thus, in order to estimate optical properties with high accuracy, a special device such as an integrating sphere is used.

Further, there exists a method for obtaining optical properties by changing the distance between a light emitter (hereinafter referred to as a "light source module") and a light detector (hereinafter referred to as a "light detection module") and measuring the amount of light detected at each distance. However, the measured amount of light may greatly change depending on the arrangement and installation conditions of the modules.

Further, there exists a method for storing a model of optical path length distribution for each layer of a measurement object that is formed of a plurality of layers, and calculating an optical absorption coefficient of a given layer based on optical path lengths measured in each of the layers, light intensity distribution, and a light intensity model (See Patent Document 1, for example).

Although methods for measuring optical properties have already been established, the existing methods are far from simple, and require a special device such as an integrating sphere. Further, in the method for obtaining optical properties by measuring the amount of light while slightly changing the distance between the light source module and the light detection module, the measured amount of light may change depending on the arrangement and installation conditions of the modules, thus resulting in unstable measurement.

RELATED-ART DOCUMENTS

Patent Documents

[Patent Document 1] Japanese Unexamined Patent Application Publication No. 2016-010717

SUMMARY OF THE INVENTION

According to at least one embodiment, an optical sensor includes a light emitter configured to irradiate a surface of an object with a plurality of non-parallel light beams, a light detector configured to detect a plurality of light beams that have been reflected within the object and have returned to the surface from a plurality of directions, a recording unit configured to store pre-calculated results of a plurality of models having different optical properties and physical structures, and a calculating unit configured to calculate a light amount ratio of the plurality of reflected light beams, and estimate an optical property of the object based on the calculated light amount ratio and the pre-calculated results.

BRIEF DESCRIPTION OF THE DRAWINGS

FIG. 1 is a schematic diagram illustrating an optical sensor according to an embodiment;

FIG. 19 is a flowchart of an estimation method 2 of optical properties;

FIG. 27 is a diagram illustrating a light source, a prism, and a detector arranged on a simulation brain model;

FIGS. 28A and 28B are diagrams illustrating simulation results (distribution of photons detected on the detector) on a per-polarized-light basis;

DESCRIPTION OF THE PREFERRED EMBODIMENTS

Figure 2A:
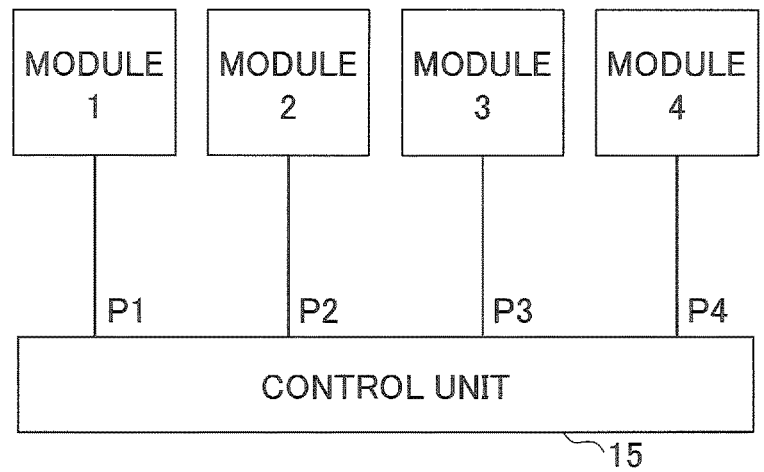
FIGS. 2A and 2B are diagrams illustrating examples of wiring schemes in which light source modules and light detection modules are connected to a control unit.

It is a general object of at least one embodiment of the present invention to provide an optical sensor that can obtain optical properties of a measurement object.

In the following, embodiments of the present invention will be described with reference to the accompanying drawings.

In the following embodiments, in order to accurately measure optical properties without being affected by the arrangement and installation conditions of modules, an optical system to be used allows light beams to be emitted from a plurality of directions onto approximately the same position, and also allows non-parallel light beams emitted from a plurality of directions to be detected. Instead of using the amount of light beams emitted from a plurality of directions, the ratio of the amounts of light beams detected in a plurality of directions is used to estimate optical properties. Thus, effects of measurement conditions and module variations can be reduced. The optical properties are estimated by comparing the ratio of the amounts of light beams detected in the plurality of directions to pre-calculated model data.

With the above configuration, it is possible to stably obtain necessary measurement data without changing the contact state between light source/light detection modules and a measurement object. Not only is excess work, such as replacement and re-arrangement of modules, eliminated, but also variations in measurement associated with changes in the arrangement and installation conditions of the modules are suppressed. Accordingly, an approximately equivalent effect to measuring at a plurality of positions can be obtained.

<Configuration of Optical Sensor>

FIG. 1 is a schematic diagram illustrating an optical sensor 10 according to an embodiment. As an example, the optical sensor 10 may be used to measure optical properties of the scalp or the skull of a human. Examples of the optical properties include a scattering coefficient and an absorption coefficient. The optical sensor 10 includes one or more light source modules 11-1 to 11-$m$ (m represents an integer of 1 or more) and one or more light detection modules 12-1 to 12-$n$ (n represents an integer of 1 or more). The light source modules 11-1 to 11-$m$ (hereinafter may be collectively referred to as a "light source module 11") are examples of light emitters. The light detection modules 12-1 to 12-$n$ (hereinafter may be collectively referred to as a "light detection module 12") are examples of light detectors. The distance between the light source module 11 and the light detection module 12 is known.

Further, the optical sensor 10 includes a control unit 15, a calculating unit 14, a recording unit 13, and a display unit 16. The control unit 15 controls the entire operation of the optical sensor 10. For example, the control unit 15 controls the operation timing of the light source modules 11 and the light detection modules 12, obtains data, transfers the obtained data to at least one of the calculating unit 14 and the display unit 16, and generates and outputs an instruction.

The recording unit 13 stores a relationship between pre-calculated optical property values and light amount ratios. The calculating unit 14 compares results obtained by the light detection module 12 to pre-calculated results, and estimates optical properties of a measurement object. The display unit 16 displays measured results. For example, operations of the calculating unit 14 and the control unit 15 may be implemented by a processor 100. The recording unit 13 may be implemented by a memory. Further, the recording unit 13 may be a memory included in the processor 100 or may be an external memory.

Figure 2B:
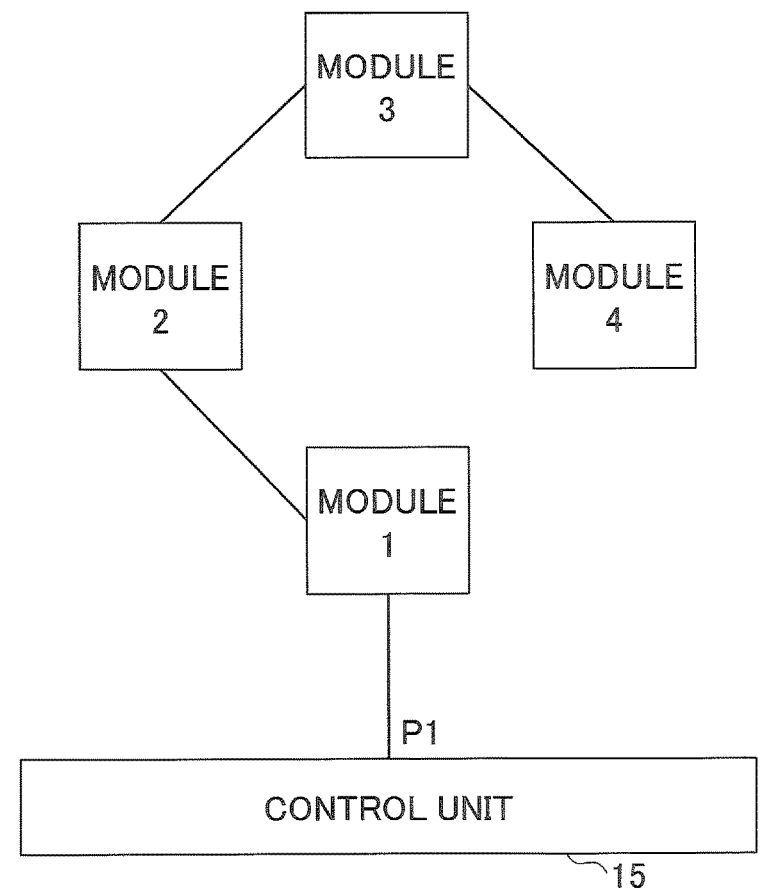

FIGS. 2A and 2B are diagrams illustrating wiring schemes in which the light source modules 11 and the light detection modules 12 are connected to the control unit 15. The light source modules 11 and the light detection modules 12 (simply described as "modules" in FIGS. 2A and 2B) may be each connected to the control unit 15 individually, as illustrated in FIG. 2A, or may be daisy-chained as illustrated in FIG. 2B. The wiring scheme illustrated in FIG. 2B is achieved through Inter-Integrated Circuit ($I^2C$) communication. In the example of FIG. 2B, two lines of a clock line and a data line are bundled together, and the multiple modules can be daisy-chained and connected to the control unit 15. In the case of the wiring scheme illustrated in FIG. 2B, the number of wires can be reduced and the connection can be simplified, as compared to the wiring scheme illustrated in FIG. 2A.

In general, when a human head is measured by using the optical sensor, an artifact may occur that causes measured data to discontinuously change when the positions of the modules are shifted. Such an artifact tends to occur when the tension of the wires acts on a contact point between the modules and the human. By bundling wires and daisy-chaining the modules as illustrated in FIG. 2B, the arrangement of the wires can be simplified, thereby reducing an effect of an artifact.

Figure 3:
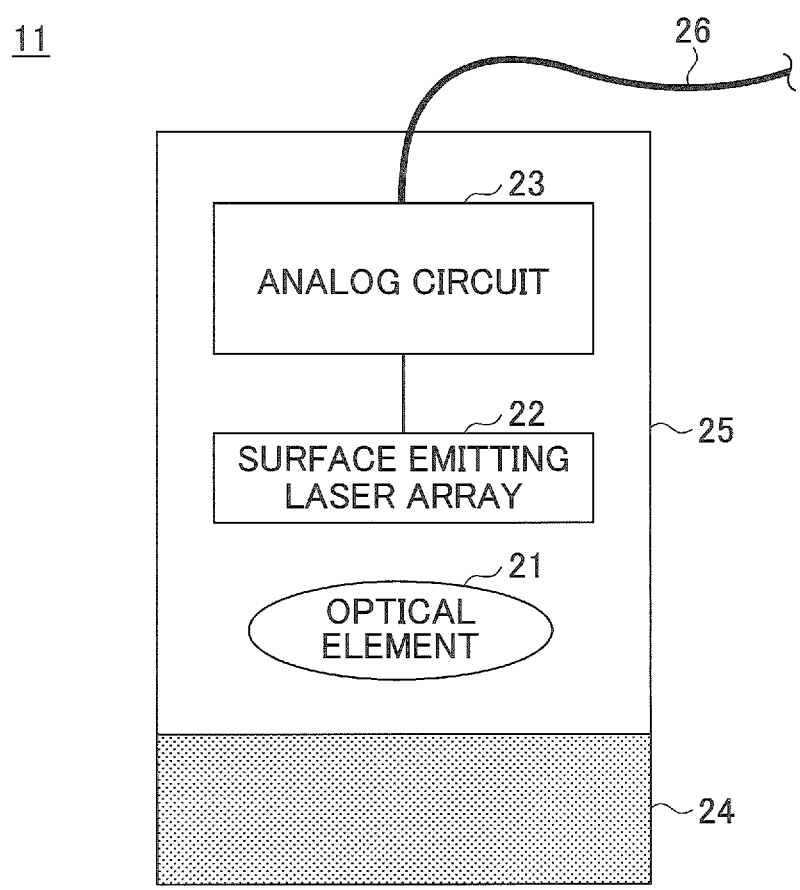
FIG. 3 is a configuration example of a light source module.

FIG. 3 is a schematic diagram illustrating the light source module 11. As described above, the optical sensor 10 causes light beams to be emitted from a plurality of directions onto approximately the same position, and the optical sensor 10 estimates optical properties based on the ratios of the amounts of light emitted from different directions.

The light source module 11 is connected to the control unit 15 by wiring 26. The wiring 26 may be individual wiring as illustrated in FIG. 2A, or I²C wiring in which a clock signal line and a data signal line are bundled.

The light source module 11 includes, for example, an optical element 21, a surface emitting laser array 22, and an analog circuit 23. These components are disposed within a housing 25 having a window 24. The analog circuit 23 outputs a drive signal for driving the surface emitting laser array 22 in accordance with a driving instruction from the control unit 15.

The surface emitting laser array 22 includes an array of light emitting elements such as vertical cavity surface emitting lasers (VCSELs), and is driven by a drive signal output from the analog circuit 23. The surface emitting laser array 22 emits light in a plurality of different directions via the optical element 21.

The window 24 is formed of a resin transparent to the wavelength to be used. The window 24 is in contact with a measurement target (an object). Light beams dispersed in a plurality of different directions via the optical element 2 pass through the window 24 and enter the surface of the object. In order to enhance the contact stability with the object, a transparent gel may be interposed between the object and the window 24.

Figure 4:
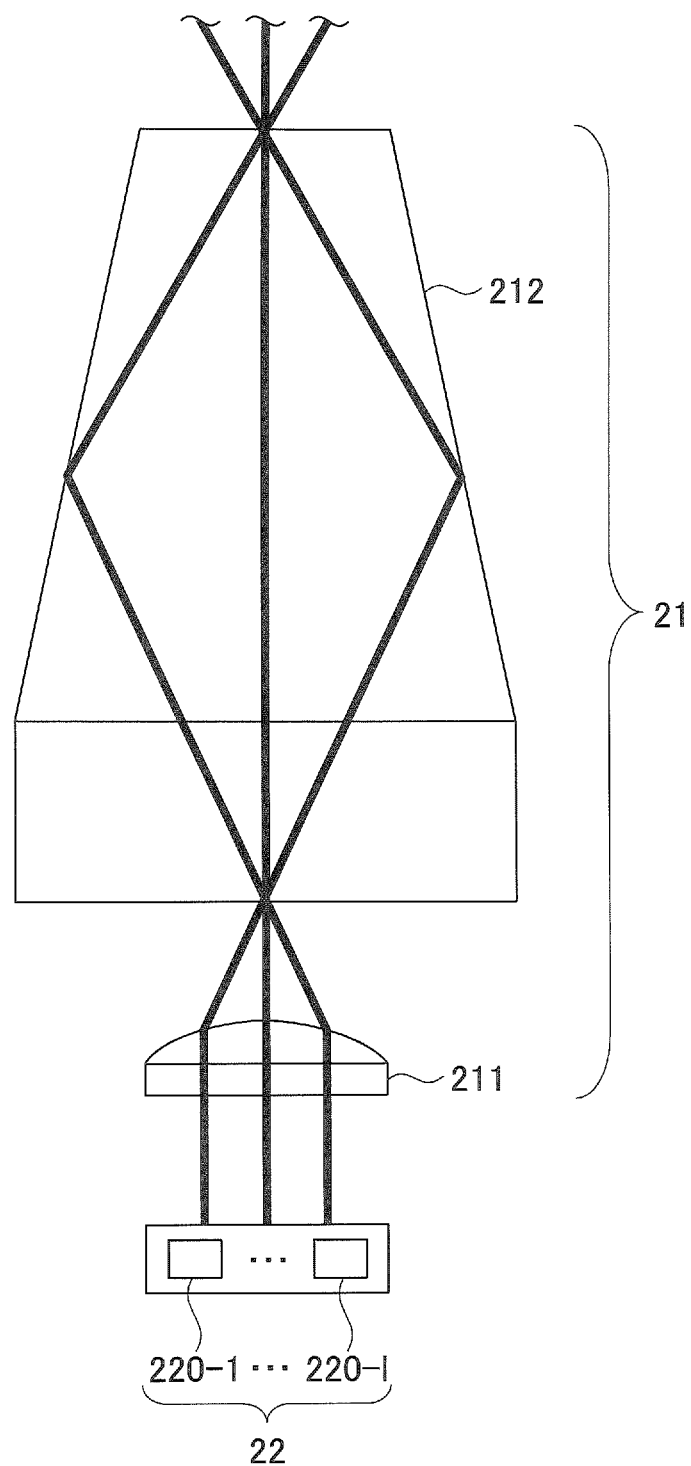
FIG. 4 is a diagram illustrating an arrangement example of an optical element used in the light source module.

FIG. 4 is a diagram illustrating an example of an arrangement relationship between the surface emitting laser array 22 and the optical element 21. The surface emitting laser array 22 includes, for example, a plurality of light emitting elements 220-1 to 220-1 arranged in a two-dimensional manner. The optical element 21 includes a lens 211 disposed facing the light emitting surface of the surface emitting laser array 22, and a prism 212 disposed on optical paths of light beams passing through the lens 211.

As illustrated in FIG. 4, the directions of light beams emitted from the surface emitting laser array 22 are approximately parallel to an optical axis of the lens 211. The traveling directions of the plurality of light beams output from the plurality of light emitting elements 220 of the surface emitting laser array 22 are changed by the output surface (convex surface) of the lens 211. However, light entering the center of the lens 211 travels straight along the optical axis of the lens 211.

Light beams whose traveling directions have been changed are reflected by the interface of the prism 212, and are emitted in different directions from the window 24 (see FIG. 3) toward the measurement object. With the above configuration, a plurality of non-parallel light beams can be emitted from the light source module 11 onto approximately the same position of the measurement surface of the object. Thus, a light emitter with multiple emission angles is implemented. For example, if a 40-channel surface emitting laser array 22 is used, it becomes possible to emit light beams in a plurality of directions in combination with the optical element 21 by causing several channels of all the channels to emit light.

Figure 5:
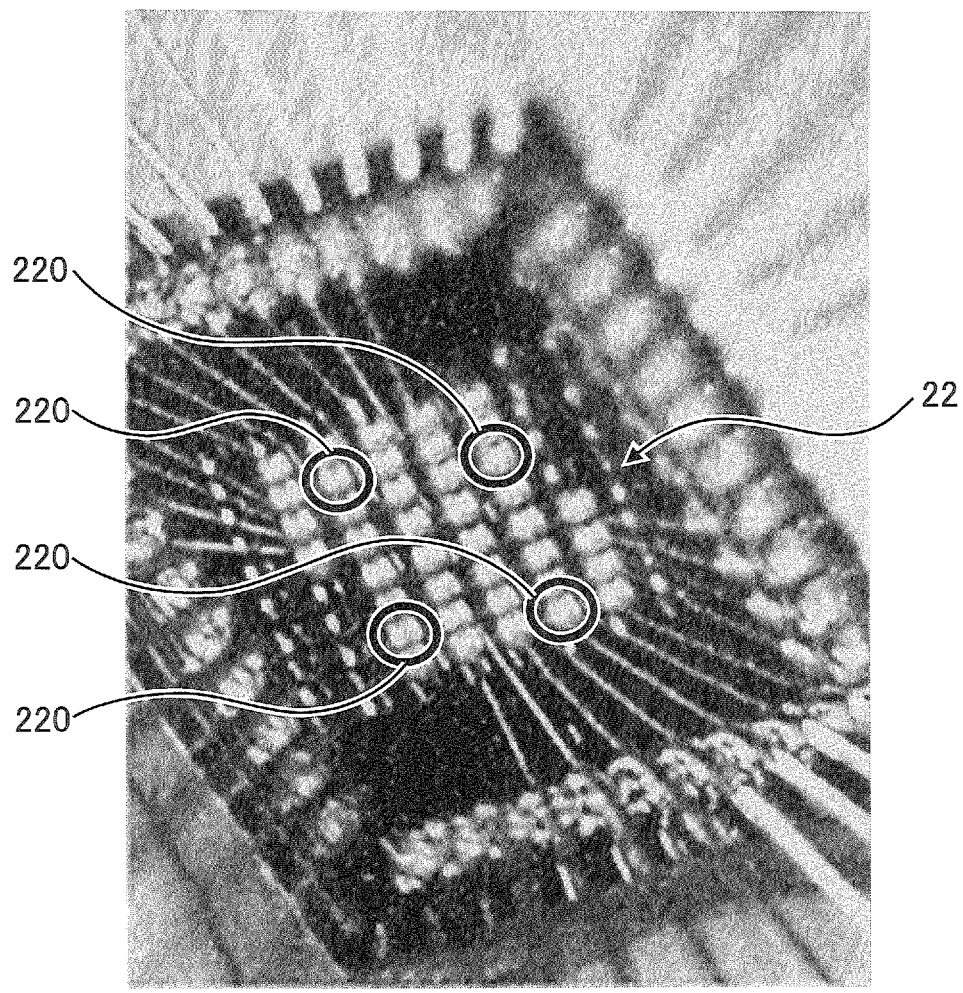
FIG. 5 is a diagram illustrating an example of light emission from a surface emitting laser array.

FIG. 5 is a diagram illustrating an example of light emission from the surface emitting laser array 22. By causing only the channels surrounded by the circles, of the plurality of light emitting elements 220 arranged in a two-dimensional manner, to emit light beams, non-parallel light beams are emitted in a plurality of directions through the lens 211 and the prism 212. The channels not used for light emission in the light source module 11 can also be used as monitor photodiodes (PDs) (light receiving elements).

Figure 6:
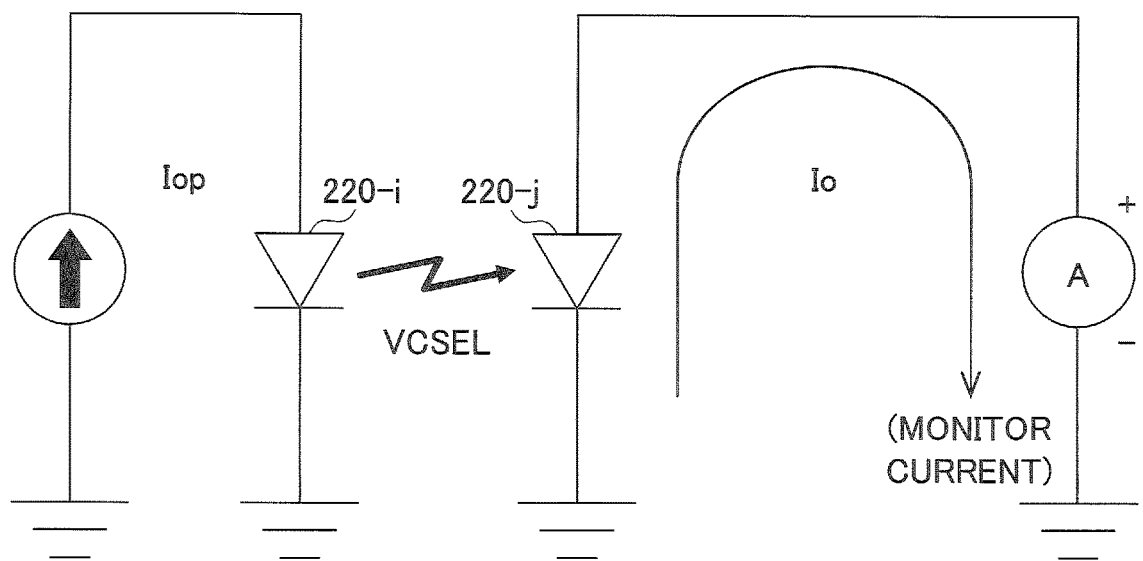
FIG. 6 is a diagram illustrating an example in which some light emitting elements of the surface emitting laser array are used as monitor PDs.

FIG. 6 is a diagram illustrating an example in which some light emitting elements 220 of the surface emitting laser array 22 are used as monitor PDs. When an operating current $I_{op}$ is supplied from the analog circuit 23 to a light emitting element 220-$i$ such as a VCSEL, light is generated by carrier generation and recombination. An adjacent light emitting element 220-$j$ is used as a light receiving element (a monitor PD) to monitor light output from the light emitting element 220-$i$. By detecting a monitor current $I_O$, the amount of light emitted from the light emitting element 220-$i$ can be monitored. For example, when the amount of output light is decreased over time, the detection result is fed back to the driving control of the light emitting element 220-$i$ via the control unit 15, and a driving current is adjusted. In this way, variations in the amount of light can be suppressed.

Further, light sources used in the light source module 11 are not limited to the VCSEL array, and edge-emitting laser diodes (LDs), light-emitting diodes (LEDs), organic EL elements, or semiconductor lasers may be used.

Figure 7:
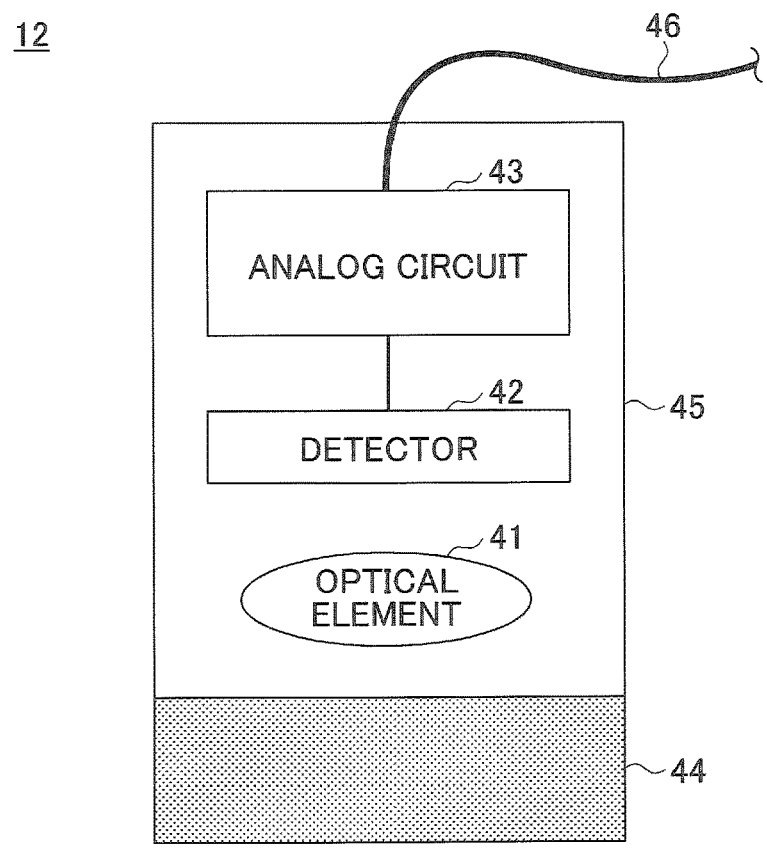
FIG. 7 is a diagram illustrating a configuration example of a light detection module.

FIG. 7 is a schematic diagram illustrating the light detection module 12. The light detection module 12 is connected to the control unit 15 by wiring 46, and detects light beams that have been emitted from the light source module 11 in a plurality of directions and have been scattered by the object.

The light detection module 12 includes an optical element 41, a detector 42, and an analog circuit 43. These components are disposed within a housing 45. The housing 45 is, for example, formed of a light-blocking material (such as a black resin). A contact member 44 that comes into contact with the object is provided at the end of the housing 45. For example, the contact member 44 is formed of an elastic body. In order to enhance the light-blocking effect, the contact member 44 may be made of black rubber.

An aperture (an opening) is formed at the end of the housing 45 and in the contact member 44. The aperture passes through the end of the housing 45 and the contact member 44. The aperture is a circular opening having a diameter of approximately 1 mm. The aperture has a function to limit the positions of light beams that enter the light detection module 12 after having been propagated through the object and emitted from the object. In the light detection module 12 as well, a transparent gel may be interposed between the contact member 44 and the object in order to enhance the contact stability with the object.

The optical element 41 may be, for example, a hemispherical lens, but any other optical element may be used as long as light can be collected in the detector 42. When light enters a light receiving element constituting the detector 42, a photoelectric current corresponding to the amount of the light flows. The photoelectric current is amplified by the analog circuit 43, and an electrical signal is supplied from the wiring 46 to the control unit 15.

Figure 8:
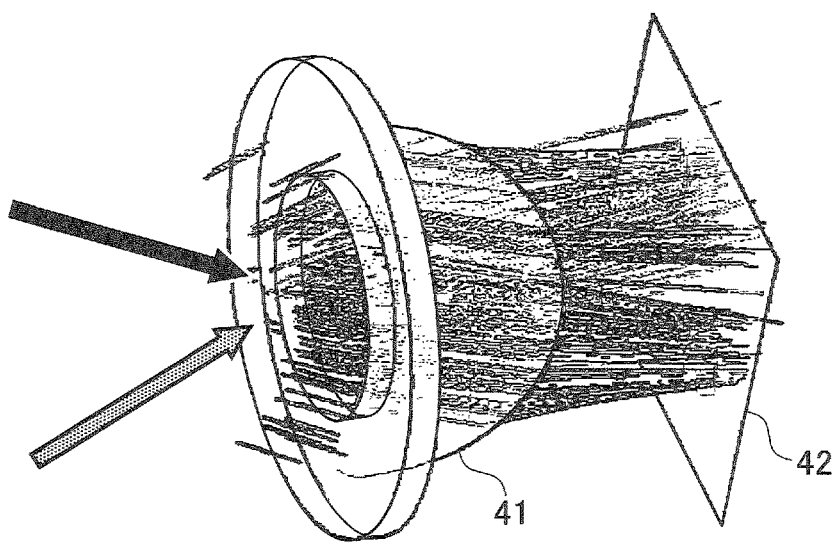
FIG. 8 is a diagram illustrating a configuration example of a detector of the light detection module.

FIG. 8 is a diagram illustrating an example of light detection by the light detection module 12. The light detection module 12 may be configured to detect light beams coming from a plurality of directions. Light beams coming from different directions are guided to different regions of the light receiving element (PD) by the optical element 41 such as a hemispherical lens. The optical element 41 is not limited to the hemispherical lens, and any other lens may be used as long as light beams coming from different directions can be guided to the detector 42, namely to different regions of the light receiving element. With the above configuration, an effect approximately equivalent to placing a plurality of light detection modules 12 can be obtained.

As a light detector, a device that uses optical fibers to measure angular distribution may be employed. However, it is generally difficult to cause light to enter each optical fiber at each angle with pinpoint accuracy. In order to allow light to enter the light receiving element in an easier way, a four-segment photodiode (PD) with four divided light receiving areas may be used.

Figure 9:
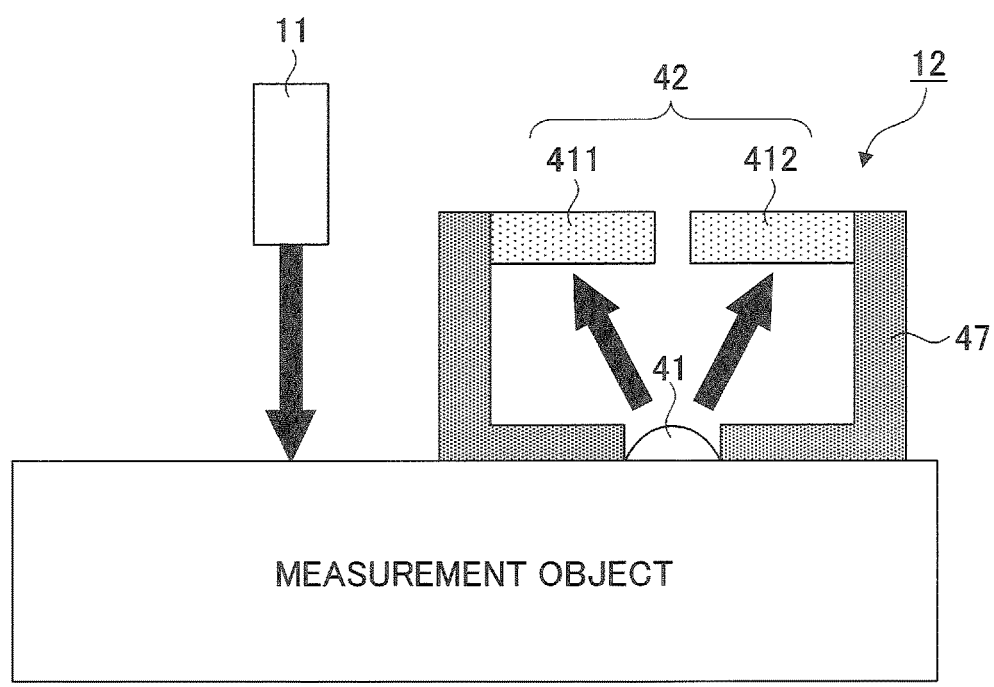
FIG. 9 is a diagram illustrating the principle of light detection.

FIG. 9 is a configuration example of the detector 42, which is a four-segment PD. Multiple non-parallel light beams output from the light source module 11 enter irradiation spots of the object, pass through different paths within the object, and enter the optical element 41 of the light detection module 12. The incident light beams are refracted in different directions by the optical element 41 on a per-incident-direction basis, and are collected into any of light receiving areas 411 and 412 of the detector 42. In FIG. 9, only the two light receiving areas are illustrated, but additional two light receiving areas are provided in a direction perpendicular to the plane of the paper. The number of division of light receiving areas is not limited to four, and any number of division of light receiving areas may be used as appropriate.

The light receiving areas 411 and 412 of the detector 42 are disposed on optical paths of light beams passing through the optical element 41, and are each connected to an operational amplifier of the analog circuit 43. Because the amount of light detected in each of the light receiving areas is very small, a two-stage amplifier configuration with relatively high magnifications is used for the operational amplifier. The first stage has a magnification of an approximate order of tens of thousands of times, and the second stage has a magnification of an approximate order of hundreds of times. By individually detecting light beams in the plurality of light receiving areas, a light detector with multiple incident angles can be implemented.

Examples of the light receiving element of the detector 42 include, in addition to a photodiode (PD), an avalanche photodiode (APD) and a single photon avalanche diode (SPAD) that is also known as a Geiger-mode APD. The APD and the SPAD are more sensitive than the PD, and thus advantageous in terms of detection accuracy.

Figure 10:
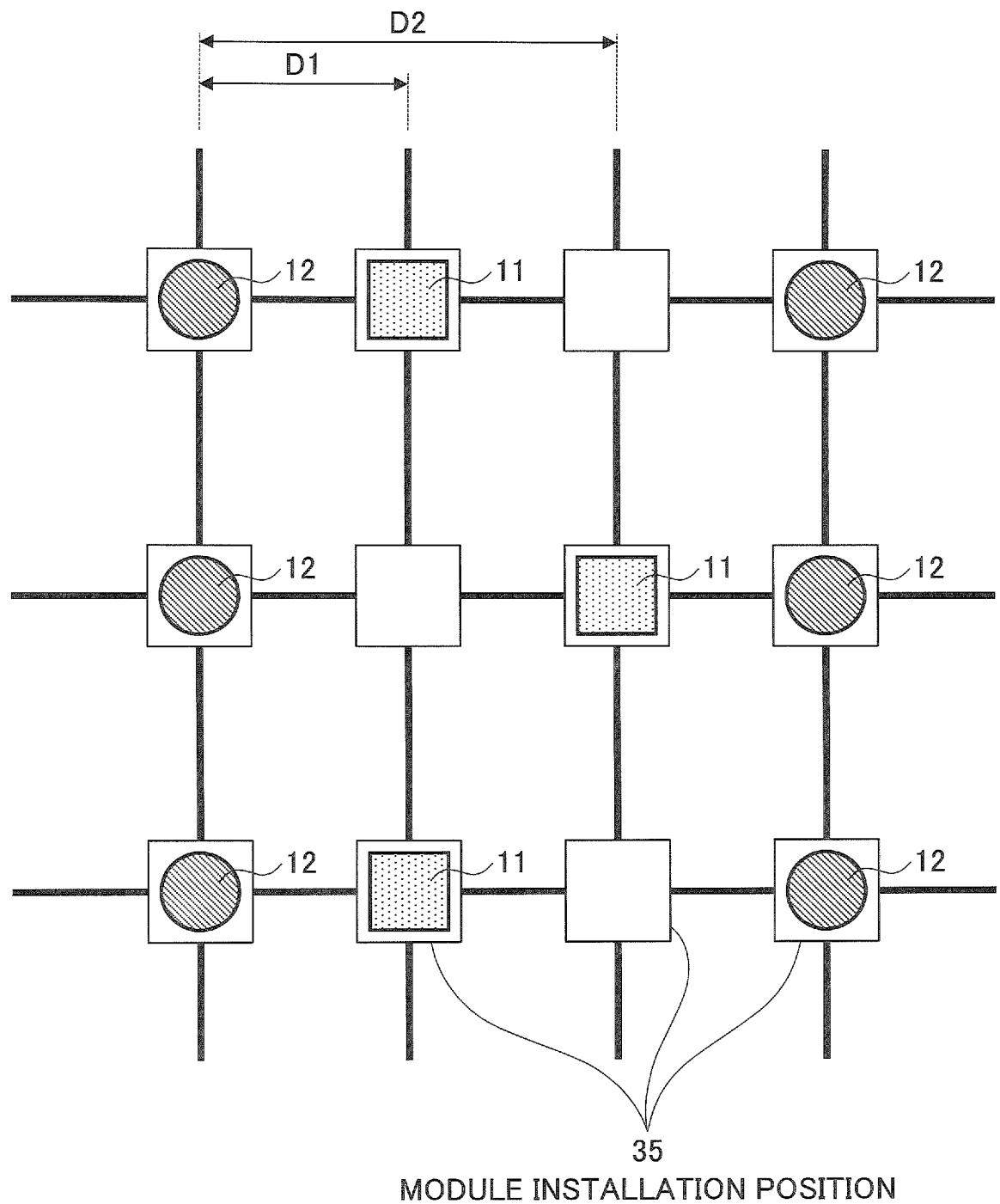
FIG. 10 is a diagram illustrating an inter-module distance adjustment mechanism.

FIG. 10 illustrates an example of an inter-module distance adjustment mechanism. It is preferable to adjust the distances between the light source modules 11 and the light detection modules 12 while constantly maintaining contact with the object. As a method for implementing the inter-module distance adjustment mechanism, module installation positions 35 greater in number than the number of the modules are provided as illustrated in FIG. 10, and the module installation positions are changed when necessary. According to the embodiments, the light source modules 11 irradiate the object with a plurality of different non-parallel light beams, and the light detection modules 12 individually detect light beams emitted from a plurality of different directions. However, an optimum inter-module distance may vary depending on the inner structure of the object. Therefore, by employing the configuration illustrated in FIG. 10, the distances between the light source modules 11 and the light detection modules 12 can be adjusted.

For example, for one object, optical properties are measured by setting the distance between a light source module 11 and a light detection module 12 to D1. For another object, it may be desirable to increase the distance between the modules. In such a case, either the light source module 11 or the light detection module 12 is rearranged to another module installation position 35. In the example of FIG. 10, the distance between the modules may be changed to D2 by rearranging the light source module 11 to the adjacent module installation position 35 on the right. The module installation positions 35 may be each provided with an adhesive pad that transmits light of the wavelength to be used.

The module installation positions 35 may be set at equal intervals in the row direction and the column direction. Alternatively, an interval in the row direction may be different from an interval in the column direction. For example, when the head is measured, an interval of the module installation positions 35 may be decreased in a region with larger curvature, and an interval of the module installation positions 35 may be increased in a region with smaller curvature.

With the above configuration, the optical sensor 10 can stably perform measurement while suppressing effects of changes in the arrangement, installation, and contact conditions of the modules.

<Method for Estimating Optical Properties>

By using the optical sensor 10, a measurement object is irradiated with light beams from a plurality of different directions, and light beams reaching the light detection modules 12 are received from a plurality of directions. Instead of using the amount of light emitted from a plurality of directions, the ratios of the amounts of light emitted from a plurality of directions are used. Thus, it becomes possible to accurately estimate optical properties while suppressing effects of changes in the measurement environment. The optical properties are estimated by comparing the ratios of the amounts of light obtained from the actual measurement to simulation results preliminarily stored in the recording unit 13. The simulation results include light amount ratio models that are preliminarily calculated by using parameters of candidate optical properties.

Figure 11:
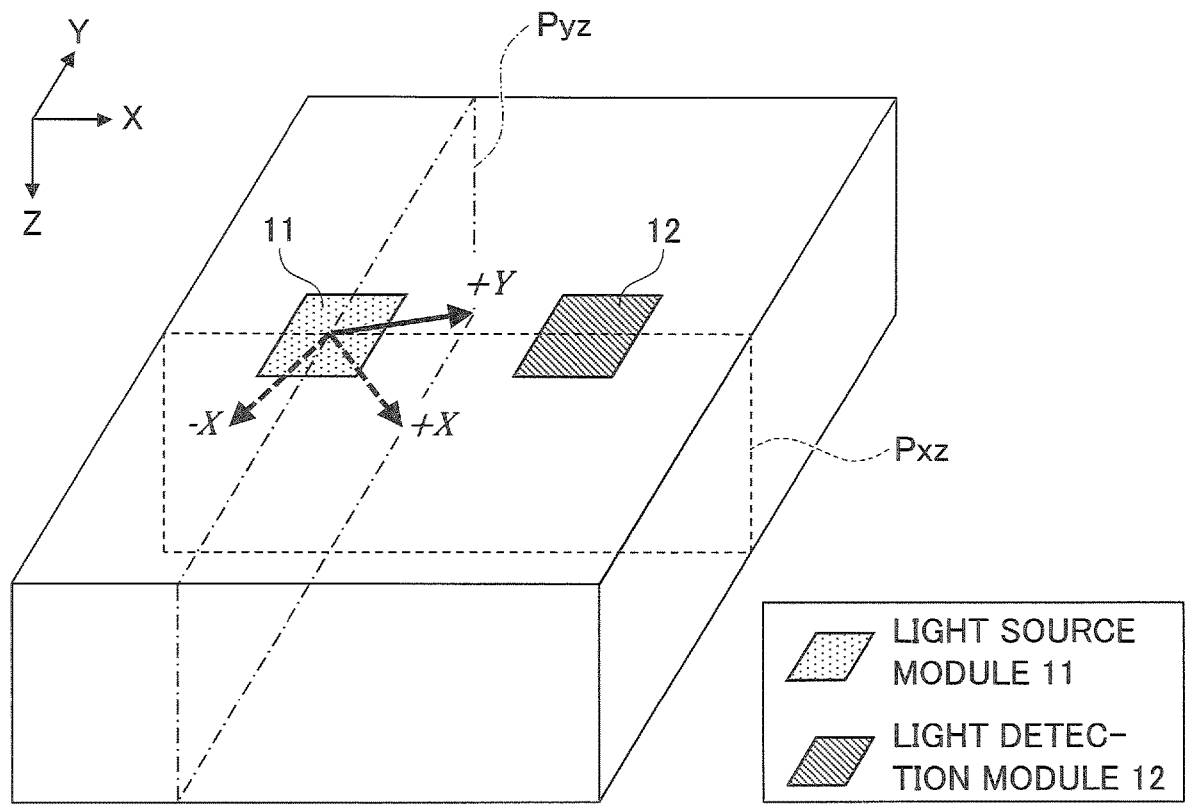
FIG. 11 is a diagram illustrating irradiation directions.

FIG. 11 is a diagram illustrating irradiation directions of the light source module 11. The direction in which light is obliquely emitted toward the inside of the object from the light source module 11 to the light detection module 12 in the XZ plane (Pxz plane) is defined as a +X direction. The direction in which light is emitted toward the inside of the object and that is opposite to the +X direction in the XZ plane is defined as a −X direction. The direction in which light is obliquely emitted toward the inside of the object in the Pyz plane perpendicular to the Pxz plane is defined as a +Y direction. The amount of detected light emitted in the +X direction, the amount of detected light emitted in the −X direction, and the amount of detected light emitted in the +Y direction are defined as I(+X), I(−X), and I(+Y), respectively. The above-described irradiation directions are merely examples, and other directions may be used as long as the ratio of the amount of light in one direction to the amount of reference light in another direction is obtained. For example, light may be emitted in the +Y direction, the −Y direction, and the +X direction, or may be emitted in two directions in each of the XZ plane and the YZ plane.

In pre-calculation, for example, Monte Carlo simulations are performed to preliminarily obtain model data. In general, as input information, a Monte Carlo simulation requires the following four optical properties and the structure (size) of a system to be calculated.

Scattering coefficient $\mu_s$

Absorption coefficient $\mu_a$

Refractive index n

Anisotropy coefficient g

In general, a Monte Carlo simulation requires a long calculation time. Thus, in order to perform estimation immediately after measurement, Monte Carlo simulations are performed in advance by using candidate parameter sets to quantitatively examine the propagation state of light, and simulated results are stored in the recording unit 13.

If a measurement object has a multi-layered structure and optical properties differ for each layer, the propagation state of light varies depending on the thickness of each of the layers. Therefore, the thickness of each of the layers is estimated prior to a simulation. In order to estimate the thickness, for example, an ultrasonic device may be used, and the thickness of each of the layers may be estimated from reflected waves. Nuclear magnetic resonance imaging (MRI) may be used when the present invention is applied to a living organism.

In continuous light measurement, the amount of light is obtained from the diffusion equation, and is characterized by the product of the scattering coefficient us and the absorption coefficient $\mu_a$, and a transmitting-receiving distance l, as indicated in formula (1).

$$\phi \propto \frac{\exp\left(-l\sqrt{3\mu'_s\mu_a}\right)}{l} \quad (1)$$

In the formula (1), $\mu_s'$ represents a reduced scattering coefficient that takes into account optical properties such as anisotropy and is expressed as $\mu_s' = \mu_s(1-g)$ (see https://annex.jsap.or.jp/photonics/kogaku/public/41-08-kaisetsu4.pdf).

The formula (1) is a rough approximation, and represents only principal terms in the photon diffusion equation for a semi-infinite homogeneous medium for a continuous-wave point source of light (see Boas, D. A., Culver, J. P., Stott, J. J., & Dunn, A. K. (2002). Three dimensional Monte Carlo code for photon migration through complex heterogeneous media including the adult human head, Optics express, 10(3), 159-170). Practically, this involves multiplication by a constant that is determined by the amplitude of the point source of light, the speed of light in the medium, and a photon diffusion coefficient. In any case, the amount of light $\phi$ depends on the product of the scattering coefficient $\mu_s$ and the absorption coefficient $\mu_a$, and these two coefficients cannot be separated.

However, by obtaining the ratio of the amounts of light for each angle of incidence, the scattering coefficient and the absorption coefficient can be identified. In general, when light is incident in a specific direction on a medium such as a living organism exhibiting high scattering, the light can be approximated as isotropically scattered from a center taken as a position to which the light had traveled by the mean free path $(-1/\mu_s')$ from an incidence point.

Figure 12:
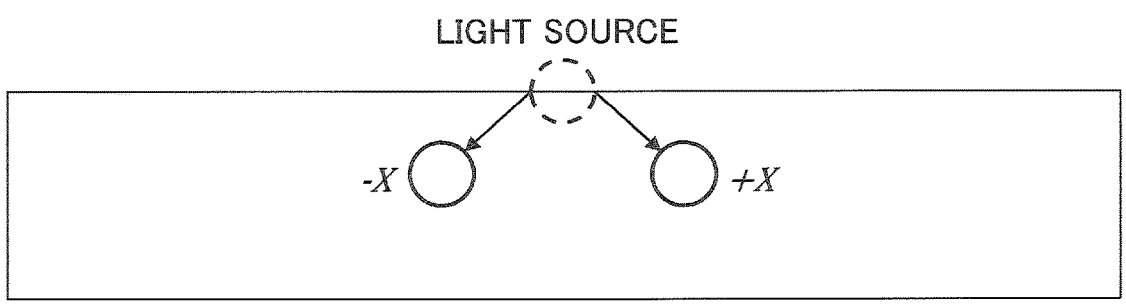
FIG. 12 is a diagram illustrating displacement of incident light due to scattering in each incidence direction.

FIG. 12 is a diagram illustrating displacement of incident light. The displacement of light due to scattering differs depending on the incidence direction. Thus, a change in the scattering coefficient appears as a change in the light amount ratio. Namely, the ratio of the amounts of light detected in irradiation directions changes depending on the value of the scattering coefficient.

For example, it is assumed that light beams are emitted in the +X direction and in the −X direction, and are detected by a light detector that is located on the +X side and has a transmitting-receiving distance l. A transmitting-receiving distance of light emitted in the +X direction is represented as $l-1/\mu_s'$, and a transmitting-receiving distance of light emitted in the −X direction is represented as $l+1/\mu_s'$.

The light amount ratio of the light beams in the two directions is represented by formula (2).

$$\ln\frac{\phi_{+X}}{\phi_{-X}} = \ln\frac{\exp\left(-(l-1/\mu'_s)\sqrt{3\mu'_s\mu_a}\right)/(l-1/\mu'_s)}{\exp\left(-(l+1/\mu'_s)\sqrt{3\mu'_s\mu_a}\right)/(l+1/\mu'_s)} \quad (2)$$

$$= \sqrt{12\mu_a/\mu'_s} + \ln\frac{(l+1/\mu'_s)}{(l-1/\mu'_s)}$$

The second term on the right-hand side of the formula (2) can be ignored if scattering is high and the mean free path $|1/\mu_s'|$ is very small as compared to the transmitting-receiving distance l Accordingly, the ratio of the scattering coefficient $\mu_s$ to the absorption coefficient $\mu_a$ is determined by obtaining the light amount ratio $\phi+X/\phi-X$.

In addition, it is possible to estimate the product of the scattering coefficient and the absorption coefficient by measuring the amount of light at a plurality of distances and calculating the ratio. The following formula (3) represents the light amount ratio when transmitting-receiving distances (sd) are l1 and l2.

[Formula 3]

$$\ln\frac{\phi(sd=l_1)}{\phi(sd=l_2)} = \ln\frac{\exp\left(-l_1\sqrt{3\mu'_s\mu_a}\right)/l_1}{\exp\left(-l_2\sqrt{3\mu'_s\mu_a}\right)/l_2} \quad (3)$$

$$= \sqrt{3\mu'_s\mu_a}(l_2-l_1) + \ln\frac{l_2}{l_1}$$

The distances $l_1$ and $l_2$ are preliminarily calculated and are thus known. Therefore, the product of the scattering coefficient and the absorption coefficient can be obtained from the light amount ratio.

Based on the formula (2) and the formula (3), values of the scattering coefficient and the absorption coefficient can be identified. Specifically, the light amount ratio of the formula (2) and the formula (3) can be obtained by detecting light emitted from a light source in the +X direction and by detecting light emitted from the light source in the −X direction.

Figure 13:
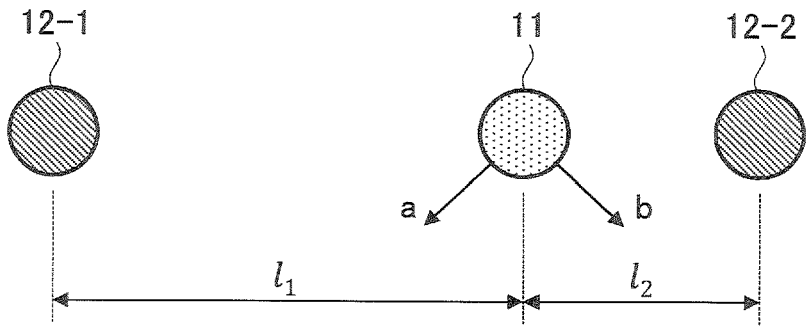
FIG. 13 is a diagram illustrating light amount measurement in different directions.

FIG. 13 is a diagram illustrating light amount measurement in a plurality of directions. A light source module 11 is disposed between light detection modules (light receivers) 12-1 and 12-2. By emitting light in the a-direction and the b-direction, the light detection modules 12-1 and 12-2 can detect light in different directions (the +X direction and the −X direction). When viewed from the light detection module 12-1, the a-direction is the positive x-axis direction with respect to the light source module 11 and the b-direction is the negative x-axis direction with respect to the light source module 11. Conversely, when viewed from the light detection module 12-2, the b-direction is the positive x-axis direction with respect to the light source module 11 and the a-direction is the negative x-axis direction with respect to the light source module 11.

As data for use in estimation of optical properties, the amount of light emitted to an object in each direction is preliminarily measured, and the light amount ratio is preliminarily stored in the recording unit 13. In measurement, the light source module 11 is disposed such that the light emitting surface of the light source module 11 is in parallel to the installation surface of the object. The light source module 11 irradiates the object with light in the +X direction, in the −X direction, and in the +Y direction (see FIG. 11) separately. The light detection module 12 detects the amount of light I(+X), the amount of light I(−X), and the amount of light I(+Y) in the respective directions, and the results are stored in the recording unit 13.

In estimation, one of the amount of light I(+X), the amount of light I(−X), and the amount of light I(+Y) stored in the recording unit 13 is used as the amount of reference light, and the ratios of the other amounts of light to the amount of the reference light are calculated. For example, the amount of light I(+X) is used as the amount of reference light, and the ratio of I(−X) to I(+X) and the ratio of I(+Y) to I(+X) are calculated. Accordingly, the ratios I(−X)/I(+X) and (+Y)/I(+X) are obtained.

By comparing these results to simulation values that are preliminarily calculated and stored in the recording unit 13, the optical properties of the measurement object are estimated. In general, the amount of detected light is affected by module variations and the installation conditions of the modules. According to the embodiments, estimation accuracy can be improved by using the ratios of the detected amounts of light.

Example 1

The scattering coefficient of a measurement sample is estimated by using the above-described optical sensor 10. The scattering coefficient is an example optical property.

Figure 14:
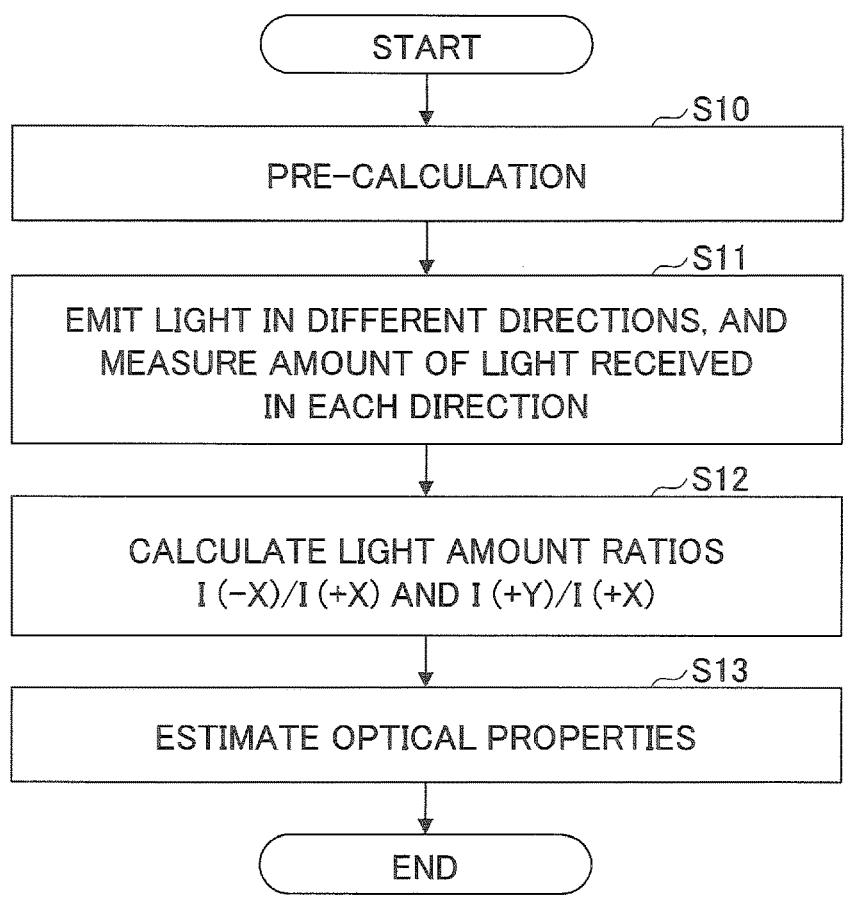
FIG. 14 is a flowchart of an estimation method of optical properties according to Example 1.
Figure 15:
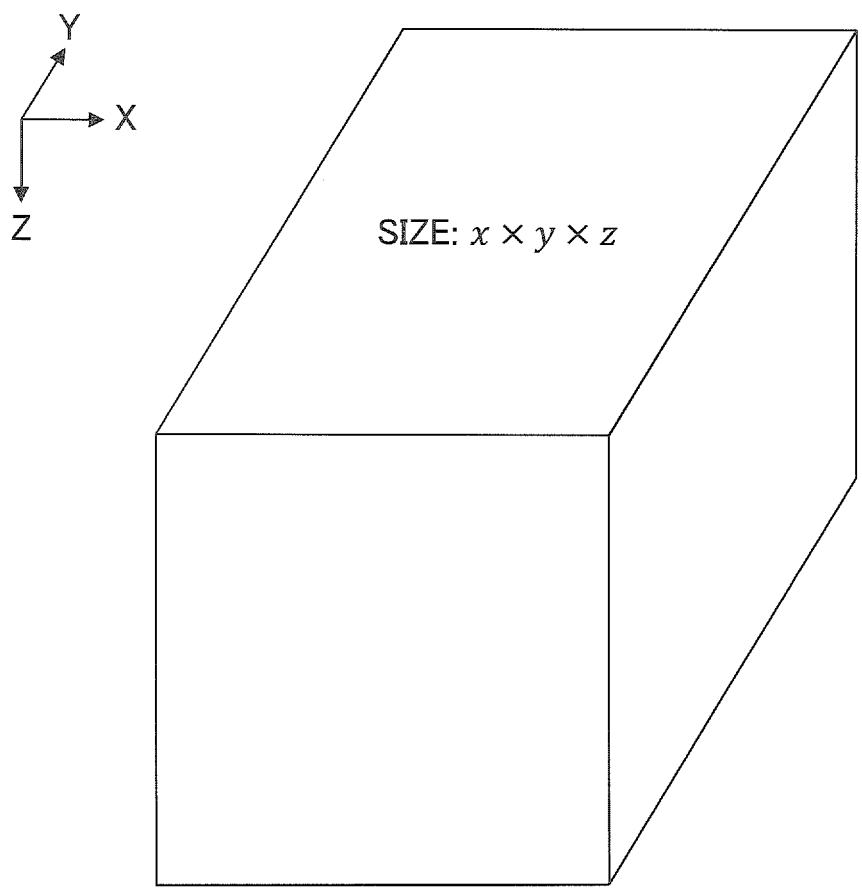
FIG. 15 is a diagram illustrating a uniform rectangular model.

FIG. 14 is a flowchart for estimating optical properties according to Example 1. First, prior to estimation, pre-calculation is performed (S10). In order to perform the pre-calculation, a model with the same size as the sample is used. For example, if a sample with the size of 121×121×60 mm³ is used, a rectangular model with the same size as the sample is used. Optical properties inside the rectangular module are assumed to be uniform. For this system, light distribution is calculated with the transmitting-receiving distance being set to 30 mm. As a calculation method, a Monte Carlo simulation is performed. For each parameter set (the light scattering coefficient, the absorption coefficient, the refractive index, and the anisotropy) in a range considered to be actually possible, the amounts of light are detected in each irradiation direction, and the ratios of the amounts of light to the amount of reference light are calculated. The calculation results are stored in the recording unit 13. The anisotropy may be referred to as asymmetry. The smaller the value of g, the more isotropic or symmetric the light is. For the refractive index and the anisotropy, standard fixed values may be used. The calculation method is not limited to the Monte Carlo simulation, and any other calculation methods may be employed.

Figure 16:
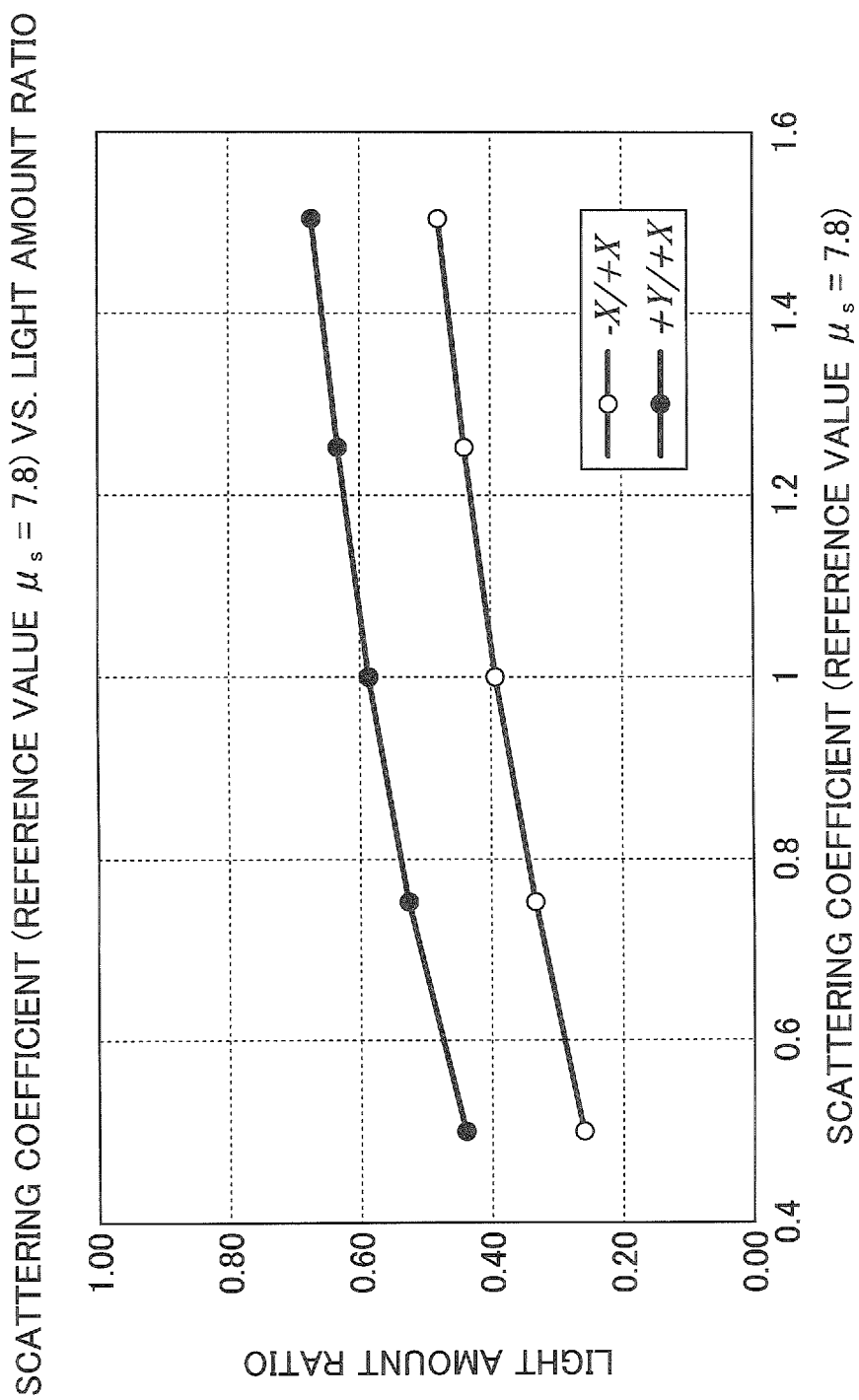
FIG. 16 is a graph illustrating changes in the ratios of the amounts of light in different directions in response to changes in a scattering coefficient.
Figure 17:
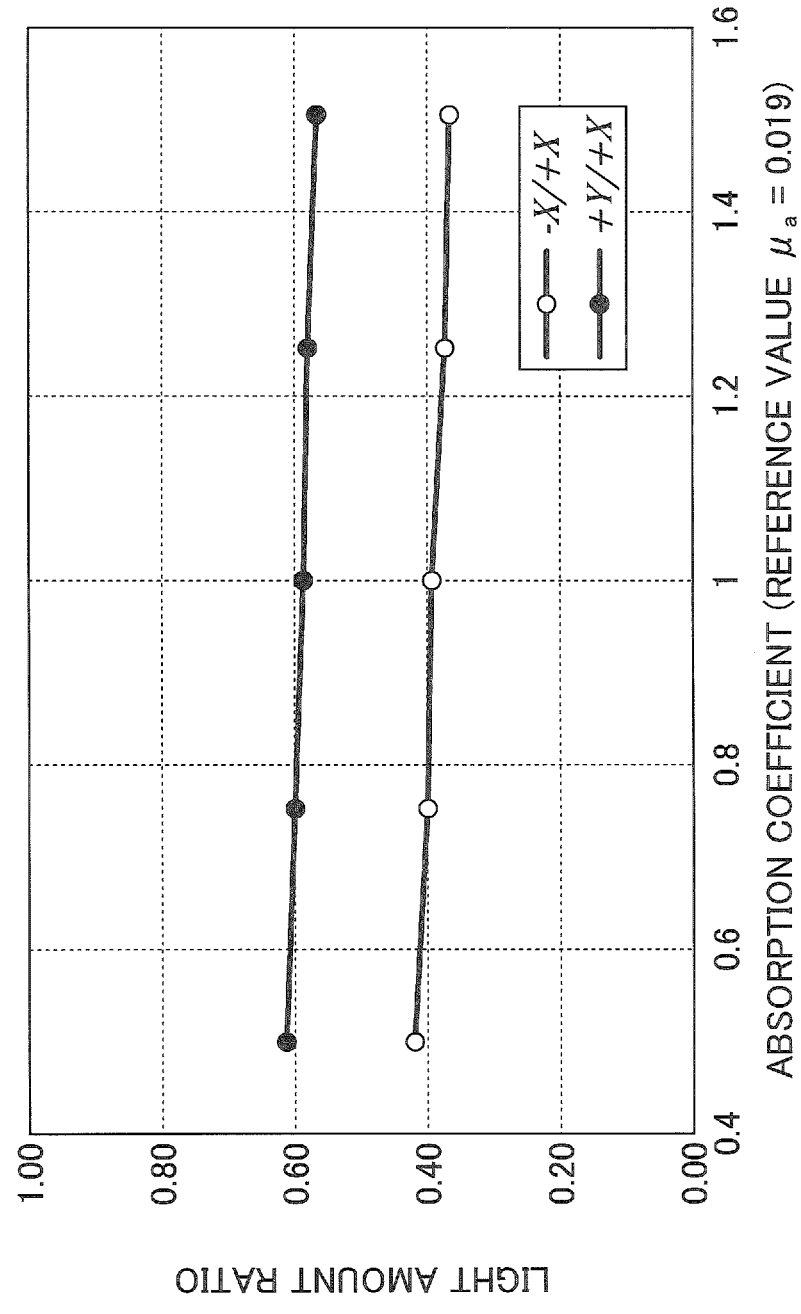
FIG. 17 is a graph illustrating changes in the ratios of the amounts of light in the different directions in response to changes in an absorption coefficient.

FIG. 16 is a graph illustrating calculation results when the scattering coefficient is changed. FIG. 17 is a graph illustrating calculation results when the absorption coefficient is changed. In both FIG. 16 and FIG. 17, the light amount ratios I(−X)/I(+X) and I(+Y)/I(+X) are calculated. The light amount ratio I(−X)/I(+X) is indicated by white circles, and the light amount ratio I(+Y)/I(+X) is indicated by black circles. The scattering coefficient indicated by the horizontal axis in FIG. 16 is expressed as the ratio when the scattering coefficient $\mu_s$=7.8 is used a reference value. The absorption coefficient indicated by the horizontal axis in FIG. 17 is expressed as the ratio when the absorption coefficient $\mu_a$=0.019 is used a reference value.

As can be seen from FIG. 16 and FIG. 17, the light amount ratios significantly change when the scattering coefficient is changed, while the light amount ratios change little when the absorption coefficient is changed. An efficient way to estimate optical properties is to first estimate the scattering coefficient based on the light amount ratios obtained from the actual measurement, and to estimate the absorption coefficient by using the formula (3). The pre-calculation results are stored in the recording unit 13.

Next, the sample is actually measured (S11). As illustrated in FIG. 11, at the time of measurement, the light source module emits light in the +X direction, in the −X direction, and in the +Y direction, and the light detection module 12 detects light emitted from the different directions. Based on the detection results, the light amount ratios I(−X)/I(+X) and I(+Y)/I(+X) are calculated (S12).

Optical properties of the sample are estimated by comparing the above calculation results to the pre-calculation results (S13). As described above, the scattering coefficient is estimated from the light amount ratios with reference to FIG. 16. After the scattering coefficient is estimated, the absorption coefficient is estimated by using the formula (3). When values of the scattering coefficient and values of the absorption coefficient are estimated for all measuring points, the process ends.

In the above-described example, random polarization light is used. However, light with different polarization directions may be used for the light sources. In general, the fluid layer (cerebrospinal fluid) and the skull have different refractive indices, and have larger refractive indices at interfaces. When light is incident on the interface between media with different refractive indices, it is known that polarization of the light causes the reflectance to change. A polarized component perpendicular to the plane of an interface when viewed in the incidence direction is called p-polarized light, and a polarized component parallel to the plane of an interface is called s-polarized light. By deliberately using polarized light, the conditions of an interface can be known in detail. The measurement using polarized light will be described in Example 3.

Example 2

Figure 18:
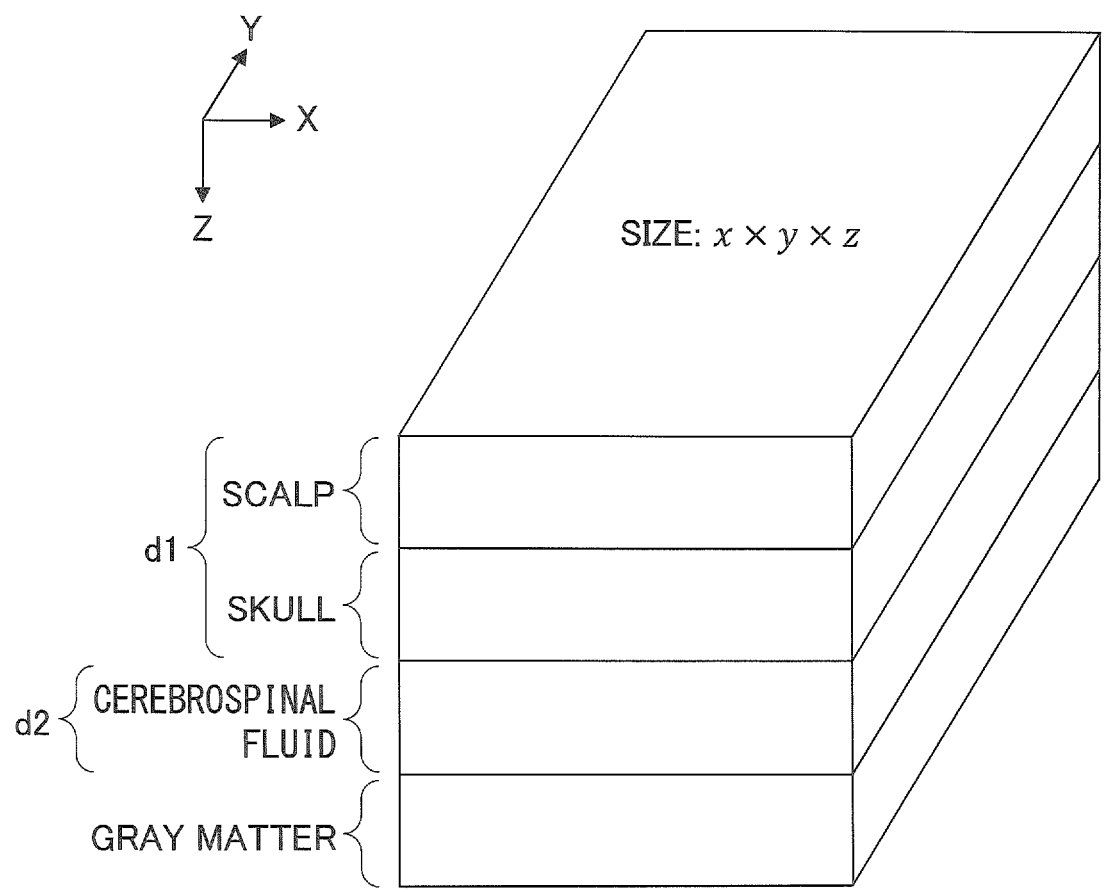
FIG. 18 is a diagram illustrating a three-layer model used in a simulation according to Example 2.

In Example 2, the optical sensor 10 is used to measure optical properties of a human head, which differ between individuals. FIG. 18 is a diagram illustrating a model used in a pre-simulation according to Example 2. FIG. 19 is a flowchart for estimating optical properties according to Example 2.

In FIG. 18, assuming that a human head is measured, a rectangular three-layer model is used. A set of a light source module 11 and a light detection module 12 is disposed as a light emitter and a light receiver. The transmitting-receiving distance is set to 30 mm as in Example 1. However, for the purpose of investigation, the transmitting-receiving distance is set to 5 mm in some measurement.

Although the human head has a four-layer structure of the scalp, skull, cerebrospinal fluid, and gray matter in order from the surface, the model illustrated in FIG. 18 has a three-layer structure. In general, the scalp layer and the skull layer are approximately identical in optical properties, and can be thus viewed as approximately the same layer. A first layer includes the scalp and the skull, and the thickness of the first layer is represented as d1. A second layer includes the cerebrospinal fluid layer that is located below the first layer, and the thickness of the second layer is represented as d2. The innermost layer located below the cerebrospinal fluid layer is the gray matter. The thickness d1 of the first layer and the thickness d2 of the second layer differ between individuals. Monte Carlo simulation are preliminarily performed by using parameters in ranges considered to be actually possible by taking individual differences into account, and the simulated results are stored. Standard values may be used for the refractive index and the anisotropy that exhibit small differences between individuals. Values of the refractive index may be determined by using, for example, the minimum deviation method, the critical angle method, the V-block method, or spectroscopic ellipsometry with high accuracy.

Table 1 indicates optical properties of each of the layers of the model illustrated in FIG. 18. As described above, in the simulations, the four parameters of the scattering coefficient, the absorption coefficient, the refractive index, and the anisotropy are used. In the three-layer model, there are 4×3 combinations. The simulation is performed by focusing only on optical properties of the first layer (scalp+skull) where most light passes through and is scattered and absorbed. For the other layers, standard data described in literature are used.

TABLE 1

| | SCATTERING COEFFICIENT $(mm^{-1})$ | ANISOTROPY | ABSORPTION COEFFICIENT $(mm^{-1})$ | REFRACTIVE INDEX |
|---|---|---|---|---|
| SCALP + SKULL | 17.5 | 0.9 | 0.017 | 1.58 |
| CEREBROSPINAL FLUID (CSF) | 0.3 | 0.0 | 0.004 | 1.33 |
| GRAY MATTER | 21.5 | 0.9 | 0.090 | 1.40 |

Table 2 indicates the range of the thickness d1 of the first layer that is greatly affected by light and that greatly differs between individuals, and the range of the thickness d2 of the second layer (cerebrospinal fluid).

TABLE 2

| | THICKNESS (mm) |
|---|---|
| FIRST LAYER | d1 = 7 to 15 |
| SECOND LAYER | d2 = 3 to 8 |

In this example, the thickness d1 of the first layer is set in the range of 7 to 15 mm, and the thickness d2 of the second layer is set in the range of 3 to 8 mm.

In FIG. 19, after the pre-simulations are recorded, the thickness d1 of the first layer of the object is measured (S21). As described above, the human head has a multi-layer structure. Thus, optical properties vary from layer to layer. When the optical sensor 10 according to the embodiment is used to measure the optical properties of the human head, the thickness of each of the layers is required to be examined. In order to examine the thickness of each of the layers, magnetic resonance imaging (MRI) or ultrasound may be employed, for example. For simplicity, average standard brain data obtained from MRI data of multiple people may be used.

When the thickness of each of the layers is estimated, the transmitting-receiving distance is set to a sufficiently small value (5 mm, for example) with respect to the thickness of the first layer, and the amount of light is measured in each direction (S22). By setting the transmitting-receiving distance to a small value as compared to the thickness of the first layer, most light passes through the first layer only, and reaches the light detection module. At least two transmitting-receiving distances are set, such that the amounts of light are measured at different distances.

Based on the measured amounts of light, the ratios of the amounts of light to the amount of reference light are calculated (S23). The calculated ratios of the amounts of light are compared to the simulation results, and the optical properties of the object are estimated (S24). Then, the process ends.

Figure 20A:
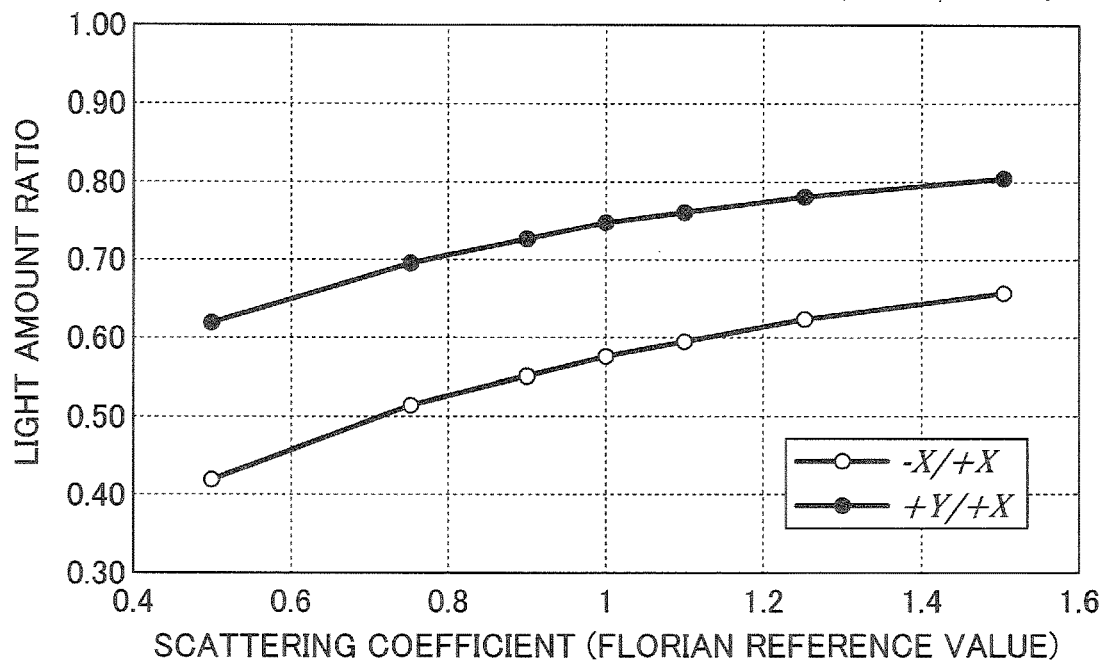
FIGS. 20A and 20B are graphs illustrating changes in the light amount ratios in the different directions in response to changes in the scattering coefficient, in which the thickness of a cerebrospinal fluid layer differs.
Figure 20B:
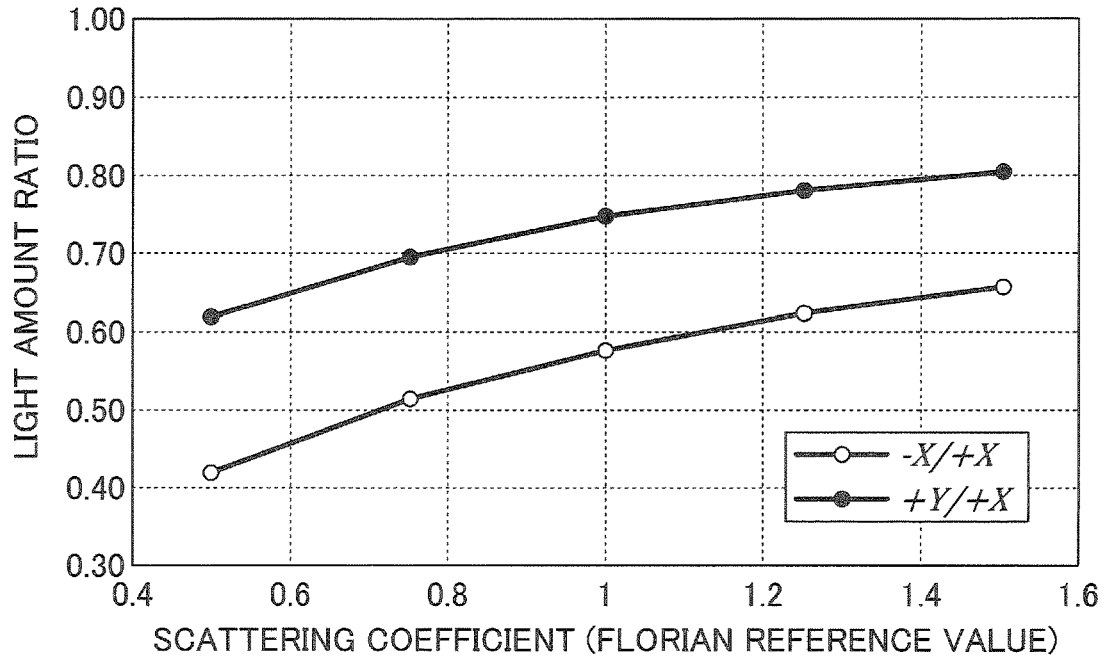
Figure 21A:
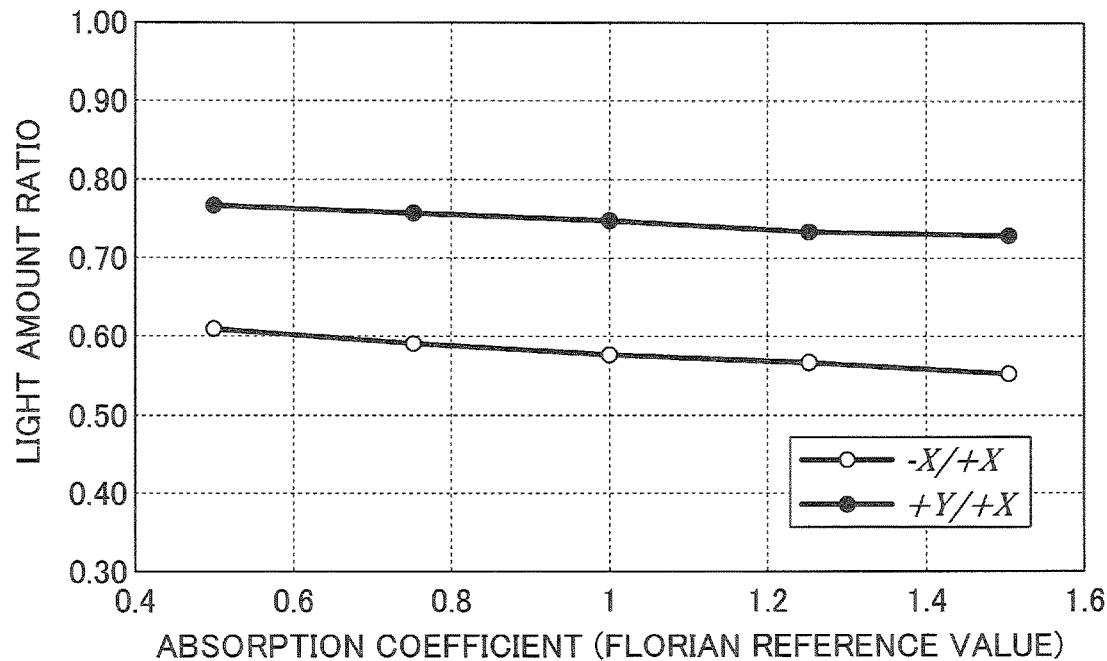
FIGS. 21A and 21B are graphs illustrating changes in the light amount ratios in the different directions in response to changes in the absorption coefficient, in which the thickness of the cerebrospinal fluid layer differs.
Figure 21B:
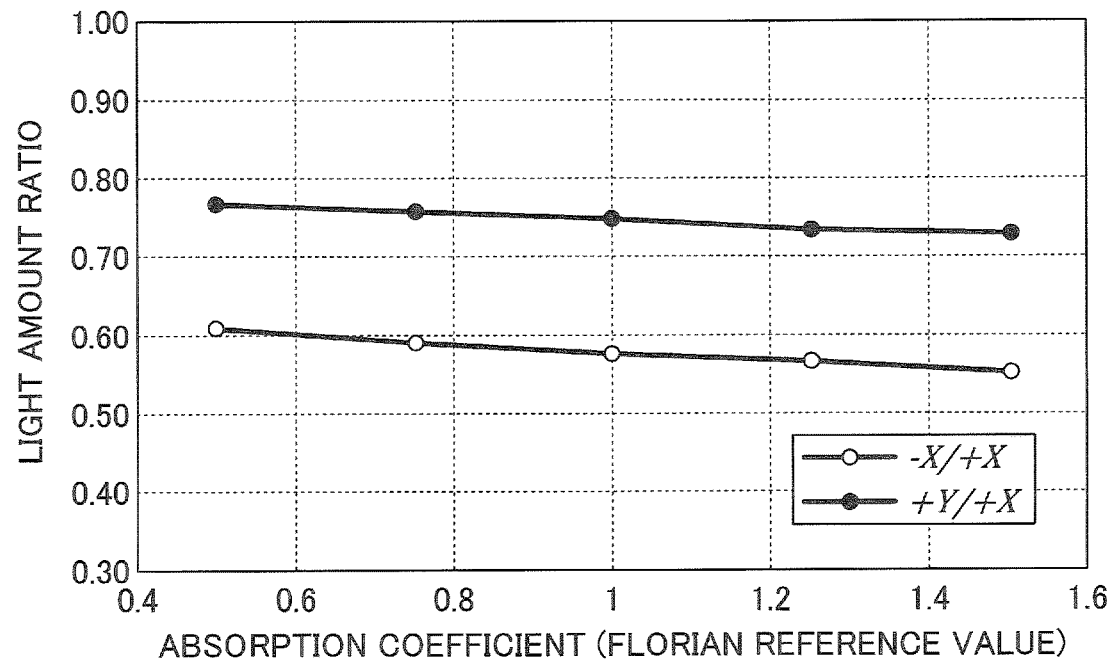

FIGS. 20A and 20B are graphs each illustrating a relationship between the light amount ratios and the scattering coefficient. In FIGS. 20A and 20B, the thickness of the cerebrospinal fluid (CSF) layer (the second layer) differs. FIGS. 21A and 21B are graphs each illustrating a relationship between light amount ratios and the absorption coefficient. In FIGS. 21A and 21B, the thickness of the CSF layer differs. More specifically, FIG. 20A illustrates a relationship between the scattering coefficient and the light amount ratios in the different directions when the CSF layer is set to 3 mm. FIG. 20B illustrates a relationship between the scattering coefficient and the light amount ratios in the different directions when the CSF layer is set to 7 mm. As in FIGS. 20A and 20B, FIG. 21A illustrates a relationship between the absorption coefficient and the light amount ratios in the different directions when the CSF layer is set to 3 mm. FIG. 21B illustrates a relationship between the absorption coefficient and the light amount ratios in the different directions when the CSF layer is set to 7 mm. In the above examples, the thickness of the first layer is set to 9 mm, and the transmitting-receiving distance is set to 5 mm.

As can be seen from FIGS. 20A and 20B and FIGS. 21A and 21B, when the transmitting-receiving distance is smaller than the thickness (d1=9 mm) of the first layer, the changes in the optical properties tend to be approximately the same even if the thickness d2 of the second layer (the CSF layer) is changed greatly. Namely, the second layer has less influence. Accordingly, in the first layer, the transmitting-receiving distance is set to a short distance, and the amounts of light are measured in a plurality of irradiation directions and at a plurality of distances. Then, the light amount ratios are calculated. Accordingly, the scattering coefficient can be determined from the pre-simulation. By using the module with multiple emission angles to estimate the scattering coefficient, the absorption coefficient can be estimated by using the formula (3) indicating the relationship between the ratio of the amounts of light beams measured at different directions and the optical properties.

Figure 22:
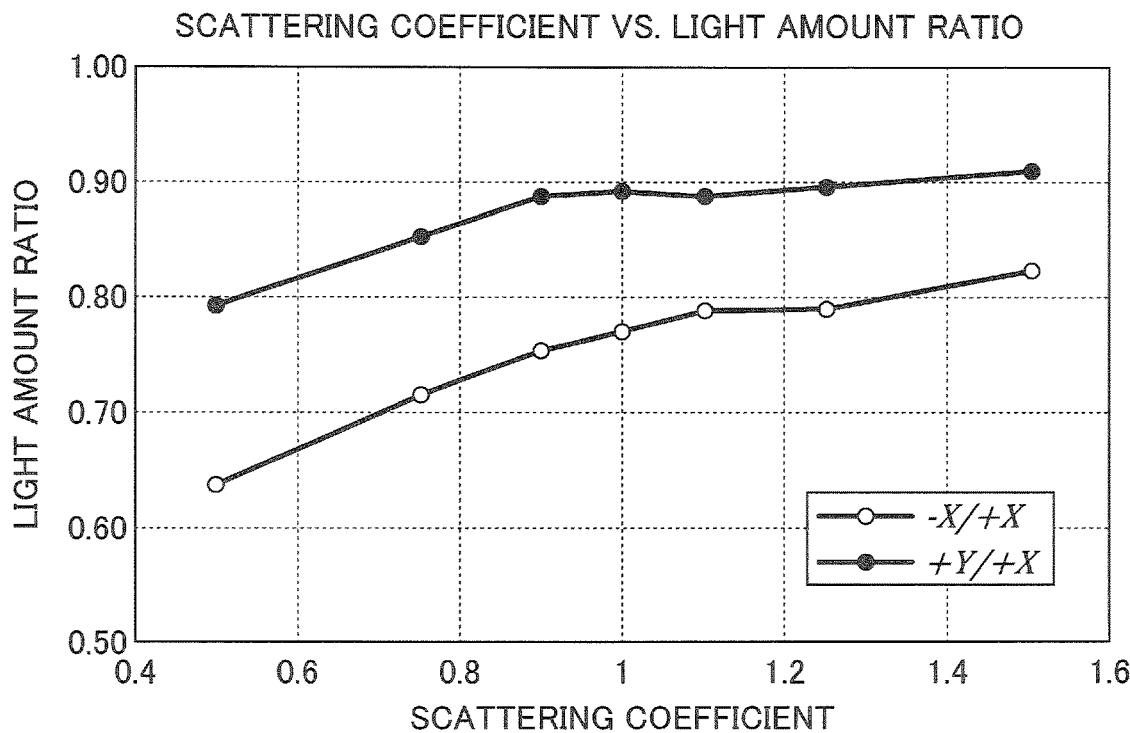
FIG. 22 is a graph illustrating changes in the light amount ratios in response to changes in the scattering coefficient, when d1 is set to 9 mm and d2 is set to 3 mm.
Figure 23:
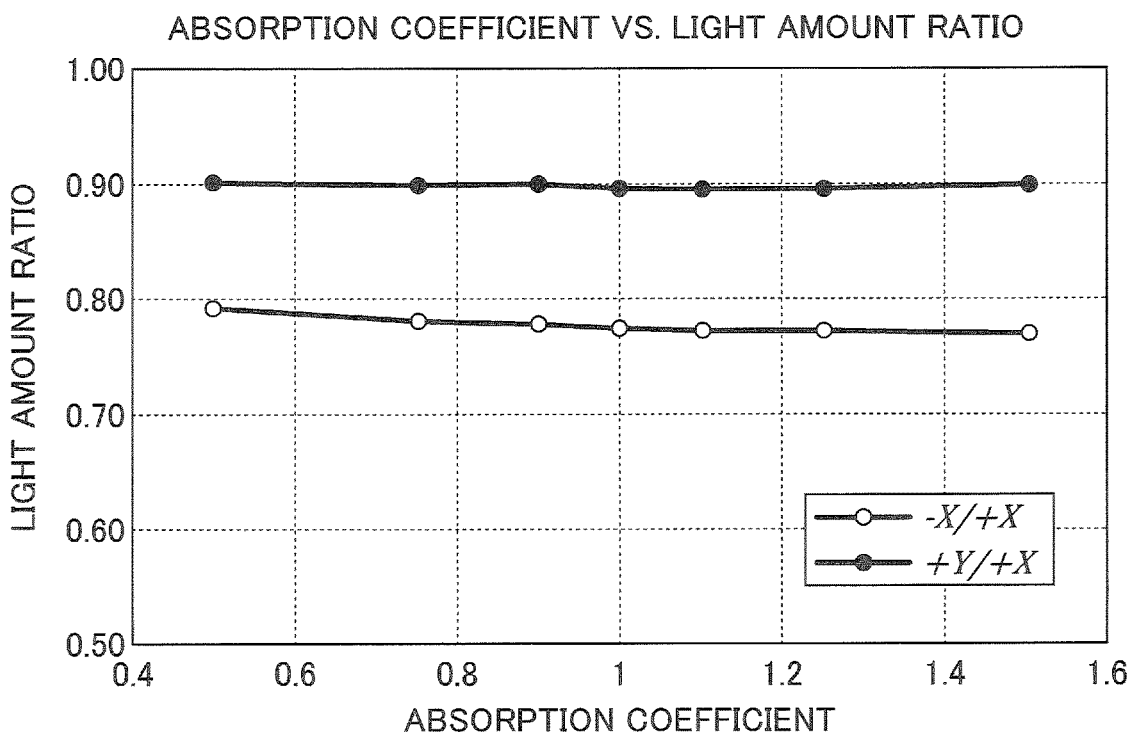
FIG. 23 is a graph illustrating changes in the light amount ratios in response to changes in the absorption coefficient, when d1 is set to 9 mm and d2 is set to 3 mm.

FIG. 22 and FIG. 23 illustrate simulation results calculated by changing the scattering coefficient and the absorption coefficient, when d1 is set to 9 mm and d2 is set to 3 mm. The scattering coefficient and the absorption coefficient are changed in a range from 0.5 times to 1.5 times, by using the values of the scattering coefficient and the absorption coefficient of the first layer (scalp+skull) in Table 1 as reference values (1).

As can be seen from FIG. 22 and FIG. 23, when the scattering coefficient is changed, the light amount ratios change greatly. Therefore, it is possible to estimate the scattering coefficient of the human head (object) by comparing the measured values (light amount ratios) to the simulation results of FIG. 22. Conversely, even if the absorption coefficient is changed, changes in the light amount ratios are small. Therefore, it is preferable to estimate the absorption coefficient based on the estimated value of the scattering coefficient. When the light amount ratios and the scattering coefficient are determined, the absorption coefficient can be estimated by using the formula (3).

Figure 24:
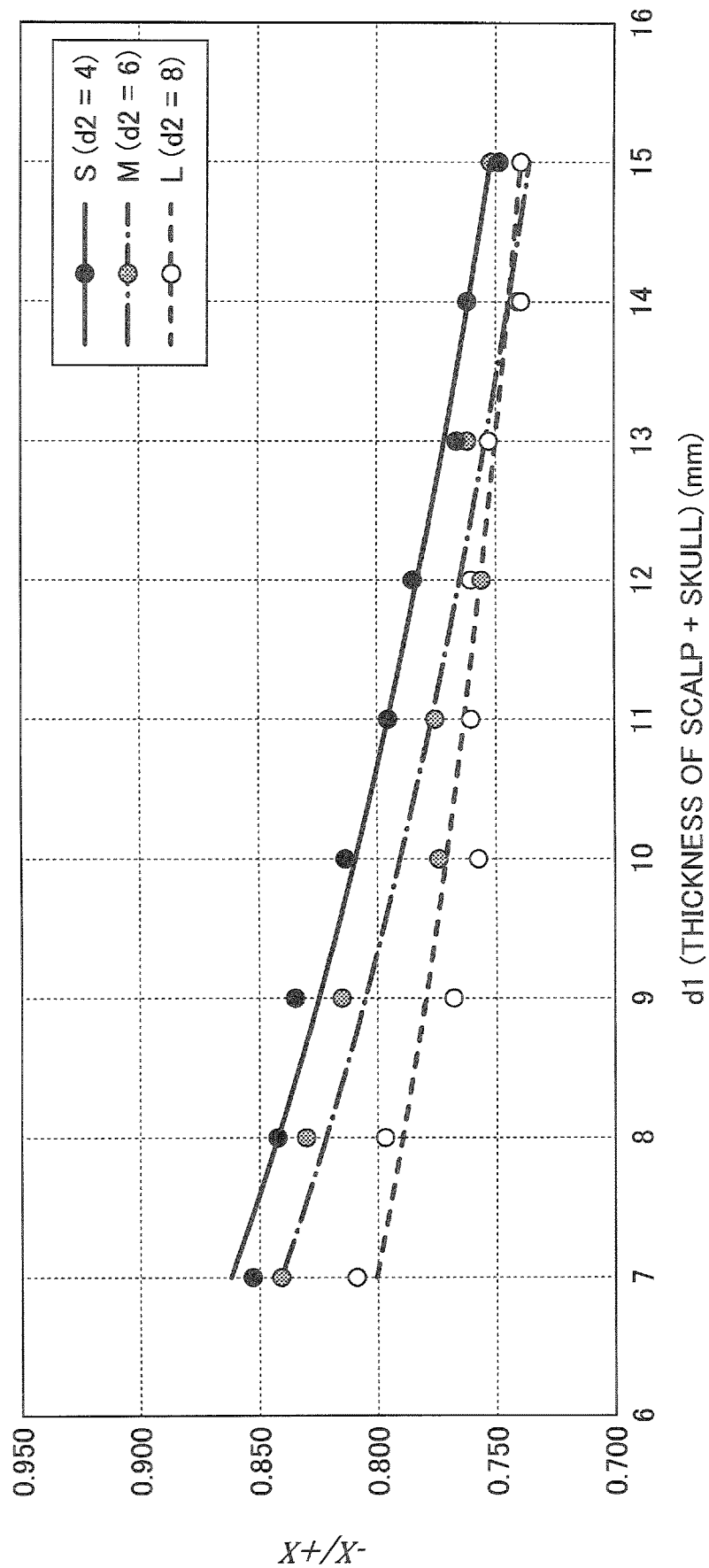
FIG. 24 is a graph illustrating changes in the light amount ratio as a function of d1 when the thickness d2 is changed.

FIG. 24 illustrates changes in the light amount ratio (−X/+X) as a function of d1 when the thickness d2 of the second layer is changed in the range from 4 mm to 8 mm. The transmitting-receiving distance is set to 30 mm. When the thickness d1 of the first layer (scalp+skull) increases, the light amount ratio does not change greatly even if the thickness d2 of the second layer differs. However, when the thickness d1 is small, the light amount ratio greatly changes depending on the thickness d2 of the second layer. Therefore, the function illustrated in FIG. 24 can be used as a model for measuring the thickness of the cerebrospinal fluid layer (second layer).

The light source module 11 and the light detection module 12 are positioned on the human head at the distance of 30 mm apart from each other, and the amounts of light beams are detected at different angles. The ratio of the measured amounts of the light beams is compared to the model data illustrated in FIG. 24. Accordingly, the thickness d2 of the cerebrospinal fluid layer can be estimated if the human skull is thin. By using the module with multiple emission angles according to the embodiment, the thickness d2 of the cerebrospinal fluid layer (second layer), which is difficult to be measured by ultrasound, can also be estimated in a simple way.

Example 3

Figure 25:
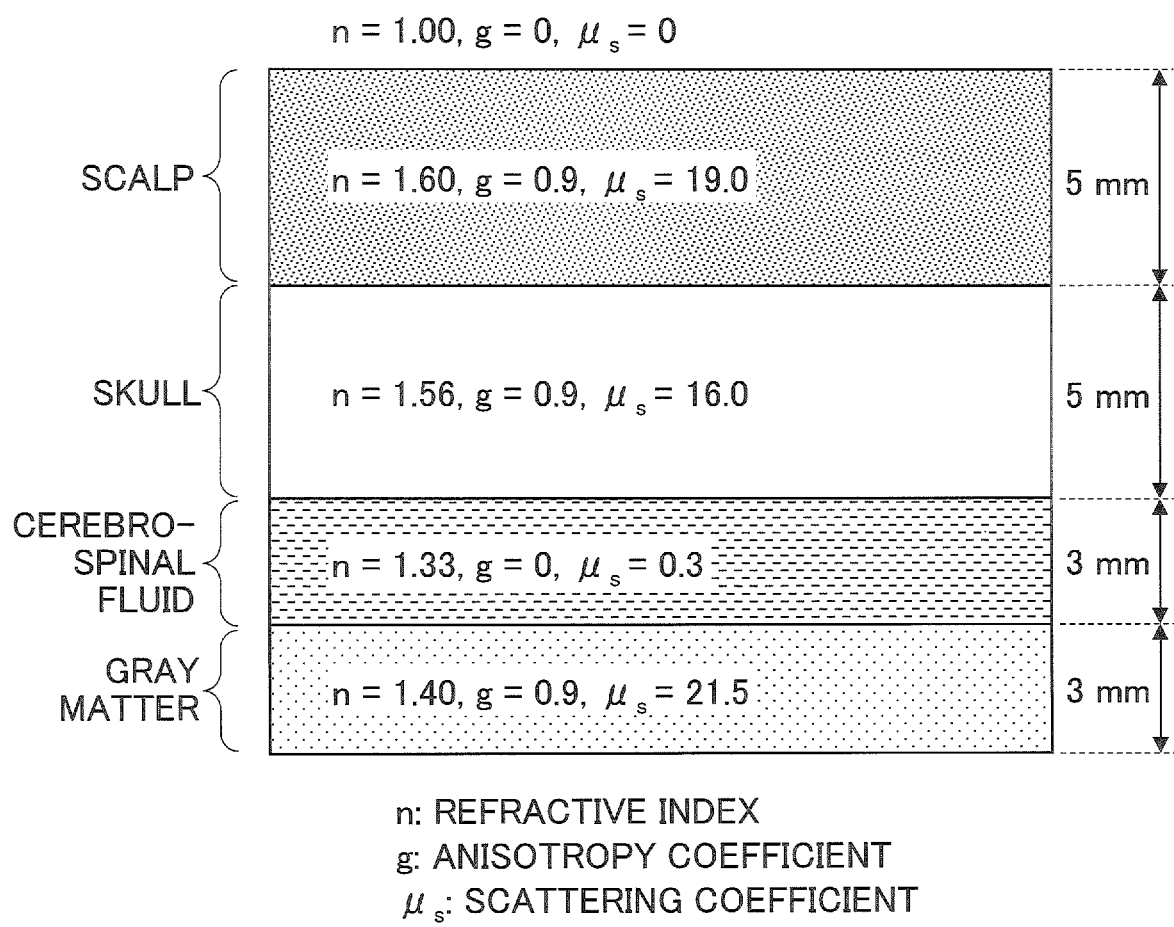
FIG. 25 is a diagram illustrating optical properties of each layer of a simulation brain model according to Example 3.
Figure 26:
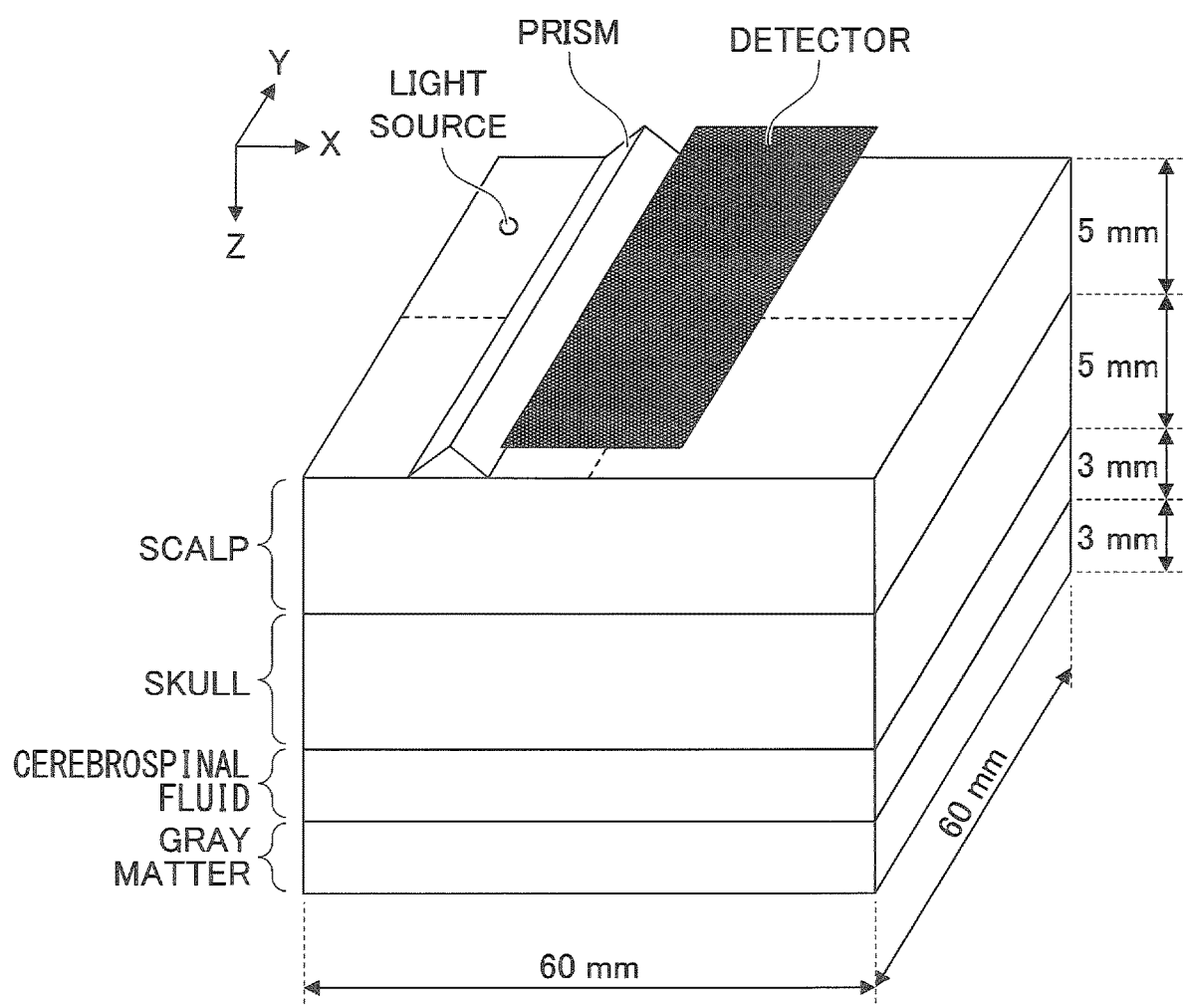
FIG. 26 is an external view of a measurement system of the simulation brain model according to Example 3.

FIG. 25 illustrates optical properties of each layer of a simulation brain model according to Example 3. FIG. 26 illustrates the appearance of a measurement system of the simulation brain model. In Example 3, the brain model is simulated by using polarized light. As illustrated in FIG. 25, the brain model according to Example 3 has a configuration in which rectangular-shaped layers of the scalp, skull, cerebrospinal fluid, and gray matter with optical properties are stacked in this order from the surface. The scalp and the skull each have a thickness of 5 mm, and the cerebrospinal fluid and the gray matter each have a thickness of 3 mm. A refractive index n, an anisotropy coefficient g, and a scattering coefficient $\mu_s$ are set as optical properties of each of the layers. In the air layer surrounding the scalp, the refractive index, the anisotropy coefficient, and the scattering coefficient are set to 0.

As illustrated in FIG. 26, a light source, a prism, and a detector are placed on the system of the brain model illustrated in FIG. 25, and an analysis is performed. There is a component below the gray matter, and light may be propagated further downward. However, the amount of light that has been reflected upon reaching a depth of at least 15 mm inside the head and has reached the detector can be ignored. Thus, all light reaching the bottom surface of the gray matter is assumed to be absorbed.

Polarized light (S-polarized light) whose direction of polarization (oscillation of the electric field) is parallel to the plane of incidence, and polarized light (P-polarized light) whose direction of polarization is perpendicular to the plane of incidence are used as light emitted from the light source. The critical angle at which light is emitted from the scalp layer to the air layer is approximately 38°. In order for light to reach the detector, the light has to be incident at an angle less than or equal to the critical angle. In this model, light output from the light source is designed to be incident at an angle of incidence of 30° with respect to the rectangular brain model or the surface of the scalp.

FIG. 27 is a diagram illustrating an interface between the air layer and the scalp layer when viewed in the X-Z plane. The prism has the same refractive index as the scalp layer, and is placed such that no gap is created between the prism and the scalp layer. The light incident surface of the prism is perpendicular to the optical axis of light emitted from the light source. The light emitted from the light source enters the scalp layer from the air layer at a desired angle without refraction.

The detector is placed at a position where light reflected by an interface of an upper layer of the brain model is emitted. The detector detects differences in the amount of reflected light between the P-polarized light and the S-polarized light. This simulation model can be used to analyze how much light propagated in a specific angular direction reaches the detector.

Typically, optical properties such as polarization and interference of light that has been incident on a material gradually disappear due to repeated light scattering. However, in the case of anisotropic scattering, circularly polarized light is not completely non-polarized even when the traveling direction of the light becomes isotropic due to scattering. Thus, visibility at a distance of approximately 10 mm inside of the human head can be expected. In a simulation according to Example 3, it is assumed that light is not scattered in the layers, such that differences between the P-polarized light and the S-polarized light can be examined.

FIGS. 28A through 30 illustrate simulation results according to Example 3. FIGS. 28A and 28B illustrate the distribution of photons detected on the detector. The distribution of photons differs between the P-polarized light and the S-polarized light. In the case of the S-polarized light, it can be seen that more light beams reach the detector, and thus a larger number of photons are detected. This indicates that the reflectance of the P-polarized light and the reflectance of S-polarized light differ in each of the layers of the brain, and the S-polarized light is reflected more than the P-polarized light.

Figure 29A:
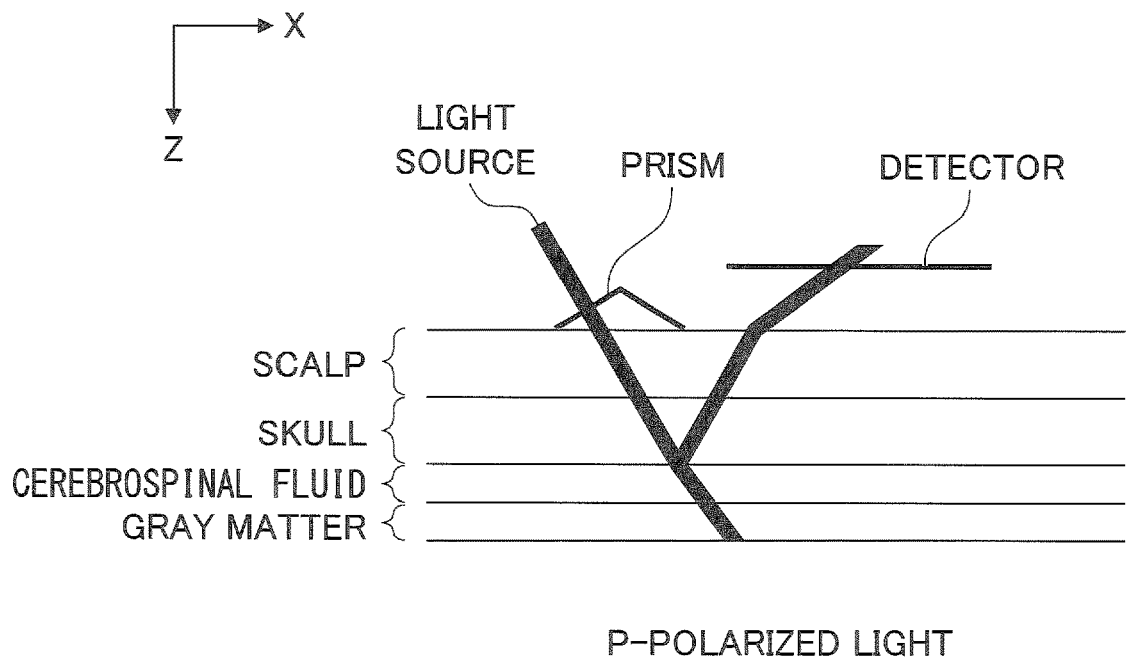
FIGS. 29A and 29B are diagrams illustrating simulation results (optical paths) on a per-polarized-light basis.
Figure 29B:
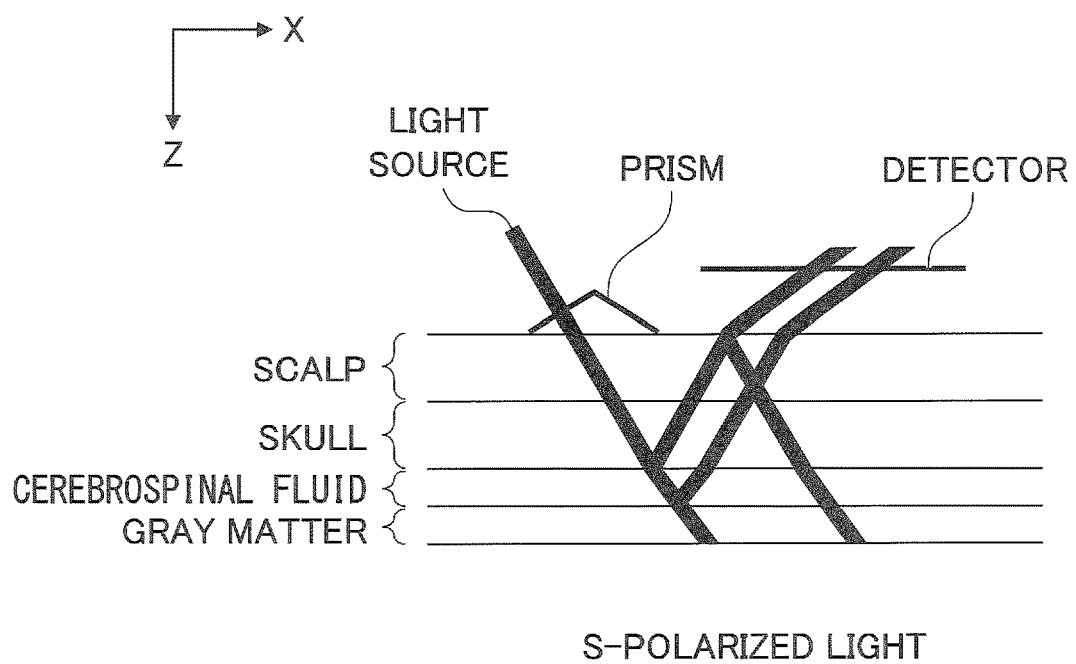

FIGS. 29A and 29B are diagrams illustrating paths of the P-polarized light and the S-polarized light that have passed through the multi-layered brain model when viewed in the XZ plane. The P-polarized light is partially reflected by the interface between the skull and the cerebrospinal fluid, is refracted by the interface between the scalp and the air layer, and reaches the detector. Components of the S-polarized light, reflected by the interface between the skull and the cerebrospinal fluid and reflected by the interface between the cerebrospinal fluid and the gray matter, reach the detector in different paths. In addition, part of the light reflected by the interface between the skull and the cerebrospinal fluid is reflected by the interface between the scalp and the air layer and returns to the interior of the brain model.

Figure 30:
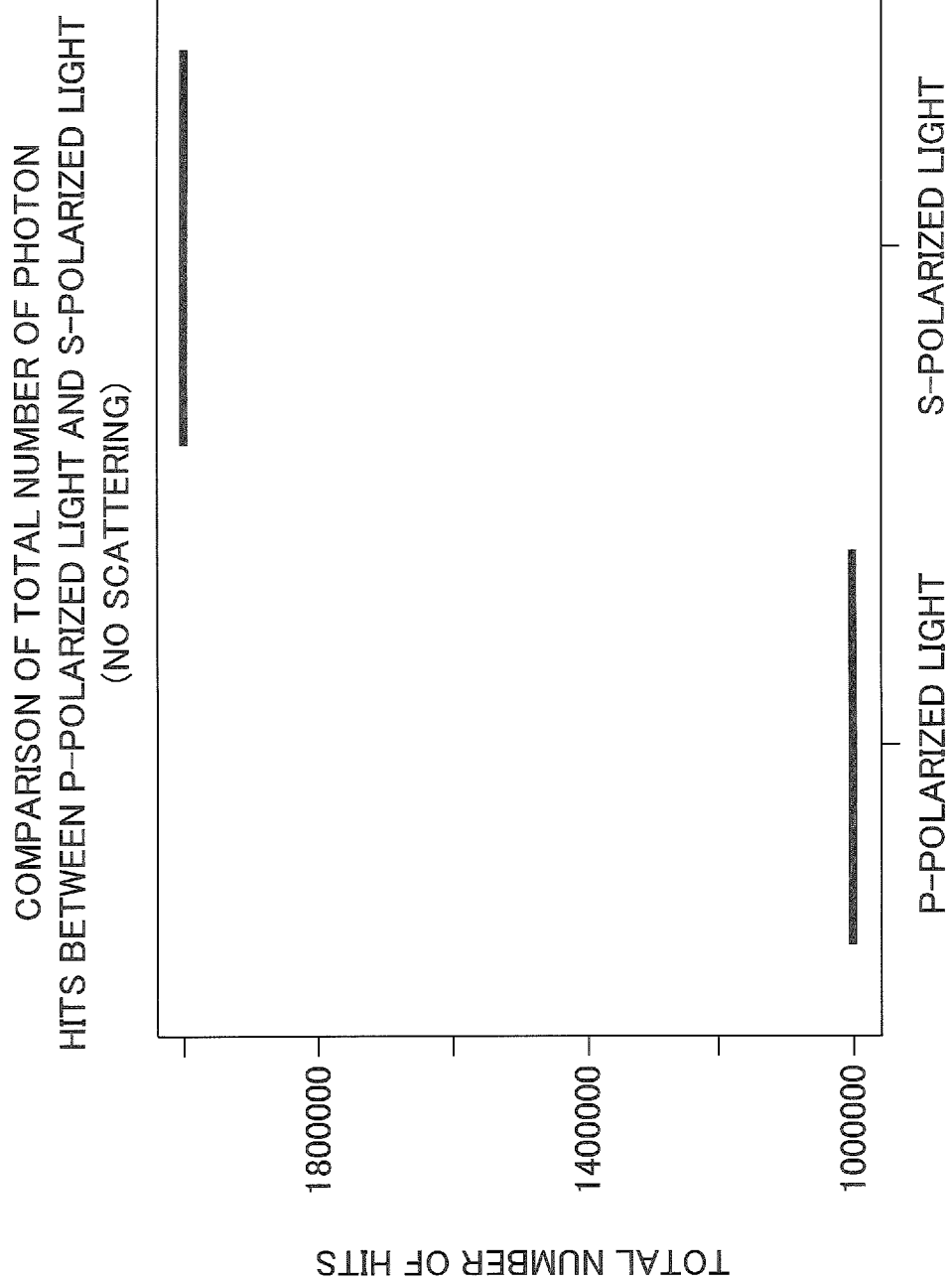
FIG. 30 is a diagram illustrating simulation results (the number of detected photons) on a per-polarized-light basis.

FIG. 30 is a box plot illustrating the number of photons that are obtained from simulations performed five times for each of P-polarized light and S-polarized light. It can be seen that approximately constant results are obtained for each of the P-polarized light and the S-polarized light.

As can be seen from the results illustrated in FIGS. 28A through 30, when light beams with different polarization directions are incident on the brain, the amounts of light beams detected by the detector become different. Thus, additional information such as chirality can be obtained in addition to analysis results as conventionally obtained by using different wavelengths.

<Application to Cancer Screening>

Figure 31A:
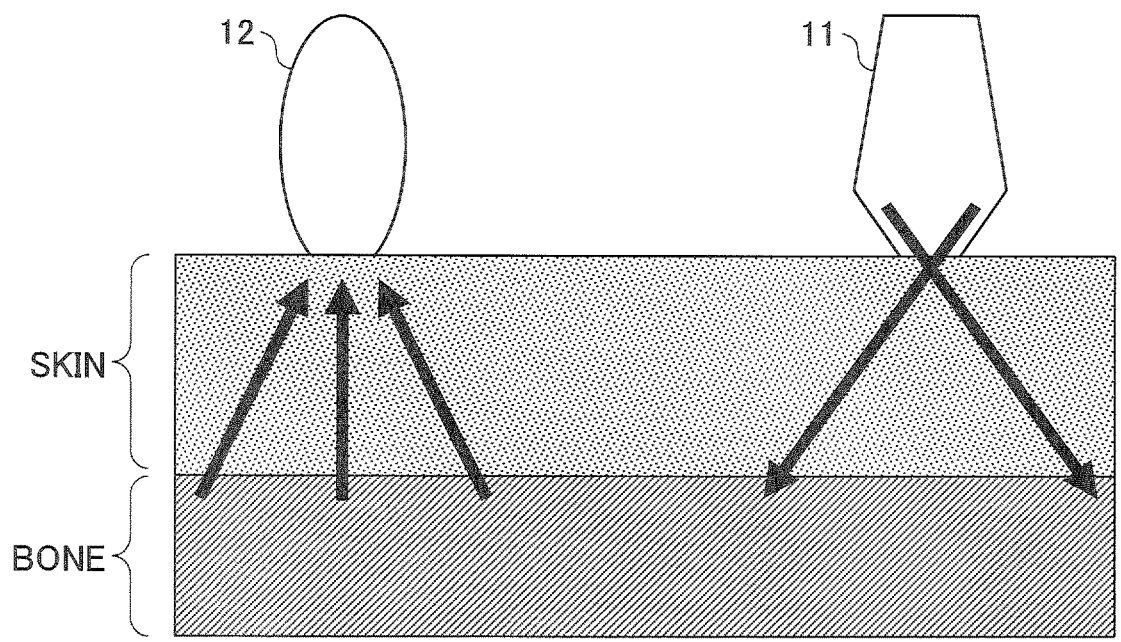
FIGS. 31A and 31B are diagrams illustrating detection of a foreign substance by using the optical sensor according to the embodiment.
Figure 31B:
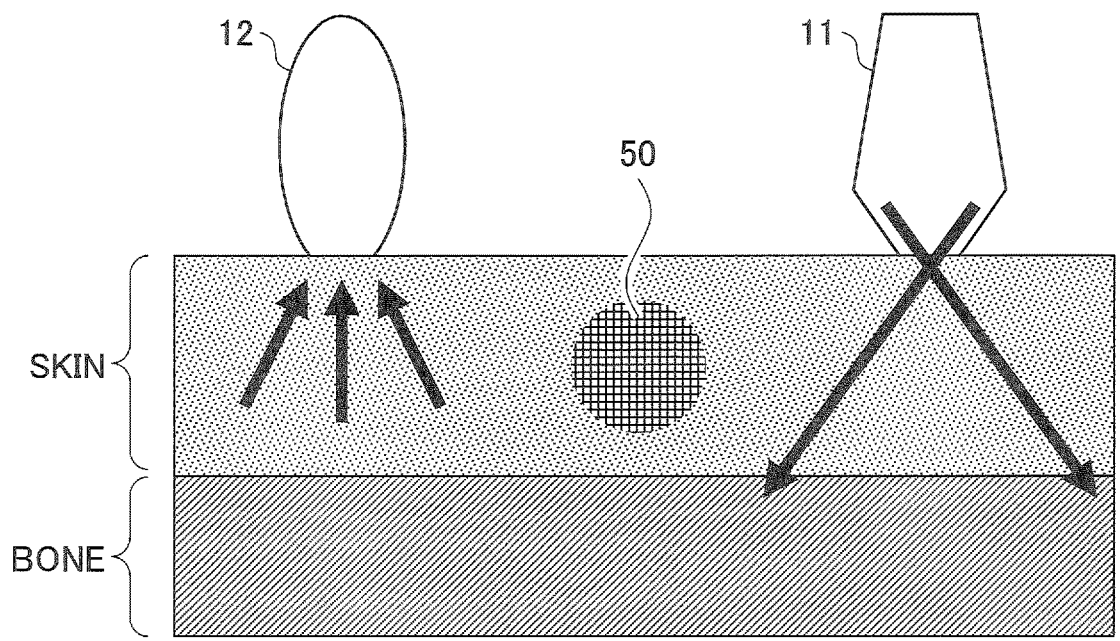

FIGS. 31A and 31B are diagrams illustrating detection of a foreign substance by using the optical sensor according to the embodiment. The optical sensor 10 according to the embodiment can be used to detect a foreign substance 50 such as cancer near the skin surface. For example, as illustrated in FIGS. 31A and 31B, a light source module 11 and a light detection module 12 are placed on the skin surface at a predetermined transmitting-receiving distance apart from each other. A human body is irradiated with a plurality of non-parallel light beams, the light detection module 12 detects light beams reflected from a plurality of directions, and the light amount ratios are calculated.

As illustrated in FIG. 31B, if cells such as breast cancer cells that are different from normal skin cells are present in a propagation path, the ratio of the amounts of light detected by the light detection module 12 becomes different from the ratio of the amounts of light detected under normal conditions as illustrated in FIG. 31A. This is because the foreign substance causes the incident light to be reflected in a different direction or to be absorbed. As a result, the amount and the propagation path of light that reaches the light detection module 12 change. Results of a simulation performed at a normal site can be preliminarily stored as a model, and the presence or absence of a foreign substance can be determined by comparing measured results to the model.

Figure 32:
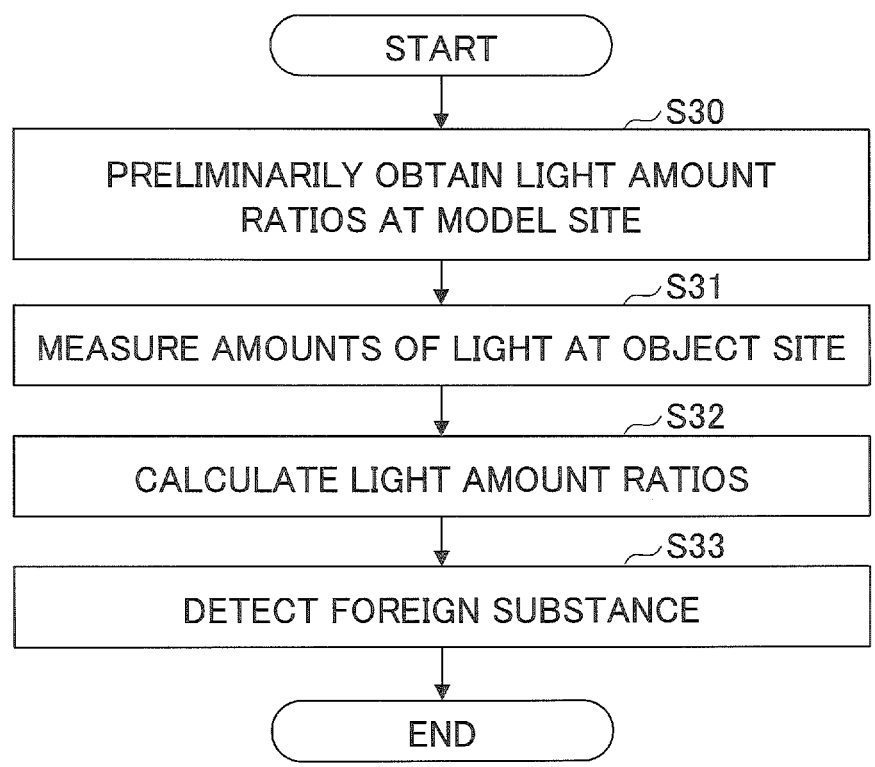
FIG. 32 is a flowchart for detecting a foreign substance.

FIG. 32 is a flowchart for detecting a foreign substance. First, the optical sensor 10 is used to preliminarily obtain the light amount ratios at a model site of normal skin cells (S30). The optical sensor 10 is used to measure the amounts of light at the same site of an object (S31). Based on the amounts of the light measured in a plurality of directions, the light amount ratios are calculated (S32). A foreign substance is detected by comparing the calculated ratios to the light amount ratios obtained at the model site (S33). In the above method, a foreign substance near the skin surface can be non-invasively detected with a simple configuration.

Although the present invention has been described based on the embodiments, the present invention is not limited to the above-described embodiments, and various modifications and variations may be made without departing from the scope of the present invention. For example, the directions in which light is emitted from the light source module 11 are not limited to the +X, −X, and +Y directions of the measurement system, and the +Y, −Y, and +X directions may be used. The amount of light used as the reference to calculate ratios is not limited to the amount of light detected in the +X direction, and any direction in which light is most stably detected may be used in accordance with the positional relationship between the light source module 11 and the light detection module 12. Further, the irradiation directions and the detection directions are each not limited to three directions. Ratios of the amounts of light beams detected in four or more directions may be used.

The display unit 16 is not necessarily included in the optical sensor 10. The results obtained from the calculating unit 14 may be displayed on an external display via a wireless or wired communication means.

In any case, optical properties can be easily estimated by comparing measured results to pre-calculated results. A light detection module detects a plurality of non-parallel light beams, thus allowing an equivalent effect to using a plurality of light receivers to be obtained. In addition, the light amount ratios are used to estimate optical properties. Thus, estimation of optical properties is less affected by the installation and arrangement conditions of the optical modules (the light source modules and the light detection modules).

When a surface emitting element array is used for the light source module, light beams can be emitted to approximately the same position from a plurality of directions. Some light emitting elements of the surface emitting element array can be used as monitor PDs to measure the amount of emitted light such that feedback control is performed. By placing the light detection modules at a plurality of different distances apart from a corresponding light source module, an additional optical property (absorption coefficient) can be easily obtained from another estimated optical property (scattering coefficient). The control unit 15 to light source modules and light detection modules are connected by $I_2C$ wiring. Thus, the number of wires can be reduced and variations in measured values due to deflection of the wires can be reduced.

According to at least one embodiment, optical properties of a measurement object can be efficiently obtained without the use of a special device such as an integrating sphere, while reducing effects of the arrangement and installation conditions of modules.

According to at least one embodiment, it becomes possible to measure optical properties without the use of a special device such as an integrating sphere, while reducing effects of the arrangement and installation conditions of modules. As compared to the conventional methods, a method for estimating optical properties can be simplified and stable measurement becomes possible.

What is claimed is:

1. An optical sensor comprising:
a light emitter configured to irradiate a surface of an object with a plurality of non-parallel light beams;
a light detector configured to detect a plurality of light beams that have been reflected within the object and have returned to the surface from a plurality of directions;
a recording unit configured to store pre-calculated results of a plurality of models having different optical properties and physical structures; and
a calculating unit configured to calculate a light amount ratio of the plurality of reflected light beams, and estimate an optical property of the object based on the calculated light amount ratio and the pre-calculated results.

2. The optical sensor according to claim 1, wherein the light detector includes a plurality of divided light receiving areas, and the calculating unit calculates the light amount ratio of the plurality of reflected light beams, the plurality of reflected light beams being detected in the plurality of divided light receiving areas.

3. The optical sensor according to claim 1, wherein the light detector includes a plurality of light detectors disposed at respective positions whose distances from the light emitter are different from each other.

4. The optical sensor according to claim 3, wherein the calculating unit calculates a ratio of amounts of light obtained at the respective positions, and estimates the optical property based on a following formula:

$$\ln \frac{\phi(l_1)}{\phi(l_2)} = \ln \frac{\exp\left(-l_1\sqrt{3\mu'_s\mu_a}\right)/l_1}{\exp\left(-l_2\sqrt{3\mu'_s\mu_a}\right)/l_2}$$

-continued $$= \sqrt{3\mu'_s\mu_a}\,(l_2 - l_1) + \ln\frac{l_2}{l_1}$$

wherein $l_1$ represents a first distance from the light emitter to one of the plurality of light detectors, $l_2$ represents a second distance from the light emitter to another one of the plurality of light detectors, $\phi(l_1)$ represents a first amount of light detected at the first distance, $\phi(l_2)$ represents a second amount of light detected at the second distance, and $\mu_s'$ represents a reduced scattering coefficient, and $\mu_a$ represents an absorption coefficient.

5. The optical sensor according to claim 1, wherein the light emitter includes a light emitting element array having a plurality of light emitting elements, and uses at least some of the plurality of light emitting elements to emit the plurality of non-parallel light beams.

6. The optical sensor according to claim 5, wherein light emission from each of the plurality of light emitting elements is individually controlled.

7. The optical sensor according to claim 5, wherein the light emitter uses the at least some of the plurality of light emitting elements to emit the plurality of non-parallel light beams, and uses other light emitting elements of the light emitting element array to monitor emission amounts of the plurality of non-parallel light beams.

8. The optical sensor according to claim 5, wherein the light emitter is a surface emitting laser array.

9. The optical sensor according to claim 1, wherein the light emitter irradiates the object with a plurality of polarized light beams whose polarization directions are different from each other.

10. The optical sensor according to claim 1, further comprising a control unit configured to control the light emitter and the light detector, wherein the control unit is connected to the light emitter and the light detector by I²C wiring.

\* \* \* \* \*